US006783680B2

(12) United States Patent
Malik

(10) Patent No.: US 6,783,680 B2
(45) Date of Patent: Aug. 31, 2004

(54) SAMPLE PRECONCENTRATION TUBES WITH SOL-GEL SURFACE COATINGS AND/OR SOL-GEL MONOLITHIC BEDS

(75) Inventor: Abdul Malik, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/001,489

(22) Filed: Oct. 23, 2001

(65) Prior Publication Data

US 2002/0150923 A1 Oct. 17, 2002

Related U.S. Application Data

(60) Provisional application No. 60/242,534, filed on Oct. 23, 2000.

(51) Int. Cl.[7] .............................................. B01D 15/08
(52) U.S. Cl. .................... 210/635; 210/656; 210/198.2; 210/502.1; 436/161; 436/178
(58) Field of Search ................................ 210/635, 656, 210/659, 198.2, 502.1; 436/161, 178; 422/70

(56) References Cited

U.S. PATENT DOCUMENTS 5,624,875 A * 4/1997 Nakanishi .................... 501/39

OTHER PUBLICATIONS

Malik, Advanced Sol–gel Column Technology for Condensed–phase Microseparation, 54 (1997).*
Abe, I.; Kameyama, K.; Wasa, T.; Chromatographia 27, 631–633 (1989).
An, M.; Haig, T.; Hatfield, P. J. Chromatogr. A 2001, 917, 245–250.
Arkles, B.; Steinmetz, J.R.; Zazyczny, J.; and Mehta, P. in Silicon Compounds: Register and Review, Huls, 1991, pp. 65–73.

Arthur, C.L.; Killam, L.M.; Buchcholz, K.D.; Pawliszyn, J.; Berg, J. Anal. Chem. 1992, 64, 1960–66.
Arthur, C.L.; Killam. L.M.; Motlagh, S.; Potter, D.W.; Pawliszyn J. Environ. Sci. Technol. 1992, 26, 979–83.
Arthur, C.L.; Pawliszyn, J. Anal. Chem. 1990, 62, 2145–2148.
Arthur, C.L.; Potter, D.W.; Buchholz, K.D.; Pawliszyn, J. LC.GC. 1992, 10, 656–61.
Atik, M.; Luna, F.P.; Messaddeq, S.H.; Aegerter, M.A. J. Sol. gel. Sci. Technol. 1997, 8, 517–522.
Augusto, F.; Koziel, J.; Pawliszyn, J. Anal. Chem. 2001, 73, 481–486.
Aylott, J.W.; Richardson, D.J.; Russell, D.A. Chem. Mater. 1997, 9, 2261–2263.
Ballesteros, E.; Cardenas, S.; Gallego, M.; Valcarcel, M. Anal Chem. 1994, 66, 628–634.
Bartle, K.D.; Woolley, C.L.; Markides, K.E.; Lee, M.L.; Hanse, R.S. J. High Resolut Chromatogr./Chromatogr. Commun 1987, 10, 128–136.
Berezkin, V.G.; Gavrichev, V.S.; Malik, A. J. Liq. Chromatogr. 1987, 10, 1707–1726.
Blomberg, L.G. J. Microcol. Sep. 1990, 2, 62–68.
Blomberg, L; Wannman, T. J. Chromatogr. 1978, 148, 379–387.
Blum, W. J. High Resolut. Chromatogr./Chromatogr. Commun. 1986, 9, 350–355.
Bouche, J.; Verzele, M. J. Gas Chromatogr. 1968, 6, 501–505.

(List continued on next page.)

Primary Examiner—Ernest G. Therkorn
(74) Attorney, Agent, or Firm—Ronald E. Smith; Smith & Hopen, P.A.

(57) ABSTRACT

A method of preconcentrating trace analytes is accomplished by extracting polar and non-polar analytes through a sol-gel coating. The sol-gel coating is either disposed on the inner surface of a capillary tube or disposed within the tube as a monolithic bed.

11 Claims, 12 Drawing Sheets

OTHER PUBLICATIONS

Buchholz, K.D.; Pawlyszyn, J. *Anal. Chem.* 1994, 66, 160–167.
Buldt, A.; Karst, U. *Anal. Chem.* 1999, 71, 1893–1898.
Cabrera, K.; Lubda, D.; Eggenweiler, H.–M.; Minakuchi, H.; Nakanishi, K. *J. High Resol. Chromatogr.* 2000, 23, 93–99.
Chaput, F.; Dunn, B.; Fuqua, P.; Salloux, K. *J. Non. Cryst. Solids.* 1995, 188, 11–18.
Chen, Z.; Hobo, T. *Anal. Chem.* 2001, 73, 3348–3357.
Chong, S.L.; Wang, D.–X.; Hayes, J.D.; Wilhite, B.W.; Malik, A. *Anal. Chem.* 1997, 69, 3889–3898.
Cortes, H.J.; Pfeiffer, C.D.; Richter, B.E.; Stevens, T.S. *J. High. Resolut. Chromatogr./Chromatogr. Commun.* 1987, 10, 446–448.
de Fatima Alpendurada, M. *J. Chromatogr. A* 2000, 889, 3–14.
de Jong, C.; Badings, H. *J. High Resolut. Chromatogr.* 1990, 13, 94–98.
de Nijs; R.C.M.; Franken, J.J.; Dooper, R.P.M.; Rijks, J.A.; de Ruwe, J.J.J.M.; Schulting, F.L. *J. Chromatogr.* 1978, 167, 231–242.
Dislich, H. in *Sol–gel Technology for This Films, Fibers, Performs, Electronics, and Specialty Shapes*, (L.C. Klein ed., Noyes Publications, Park Ridge, NJ, USA, 1988), pp. 50–79.
Doesey, J.G.; Lister, A.S.; Wright, P.B.; Wendelken, S.C.; Chester, T.L. *Proc. 19$^{th}$ International Symposium on Capillary Chromatography and Electrophoresis*, Wintergree, VA, USA, May 18–22, 1997, pp. 62–63.
Dulay, M.T.; Kulkami, R.P.; Zare, R.N. *Anal. Chem.* 1998, 70, 5103–5107.
Dutoit, D.C.; Schneider, M.; Baiker, A. *J. Catal.* 1995, 153, 165–176.
Eisert, R.; Pawliszyn, J. *Anal. Chem.* 1997, 69, 3140–3147.
Engelhardt, H.; Cunat–Walter, M.A. *J. Chromatogr.* 1995, 716, 27–33.
Fabes, B.D.; Uhlmann D.R. *J. Am. Ceram. Soc.* 1990, 73, 978–988.
Fields, S.M. *Anal. Chem.* 1996, 68, 2709–2712.
Fujimoto, C. *J. High Resol. Chromatogr.* 2000, 23, 89–92.
Gbatu, T.P.; Sutton, K.L.; Caruso, J.A. *Anal. Chim. Acta* 1999, 402, 67–79.
Gou Y.; Pawliszyn, J. *Anal. Chem.* 2000, 72, 2774–2779.
Gou, Y.; Eisert, R.; Pawliszyn, J. *J. Chromatogr. A* 2000, 873, 137–147.
Gou, Y.; Tragas, C.; Lord, H.; Pawliszyn, J. *J. Micro Sep.* 2000, 12, 125–134.
Grob, K. Jr.; Grob, G.; Grob, K.; 1978, 156, 1–20.
Grob, K.; Grob, G.; Blum, W.; Walther, W. *J. Chromatogr.* 1982, 244, 197–204.
Guo, Y.; Colon, L.A. *Anal. Chem.* 1995, 67, 2511–2516.
Guy, Y.; Colon, L.A. *Chromatographia* 1996, 43, 477–483.
Guo, Y.; Colon, L.A. *J. Microcol. Sep.* 1995, 7, 485–491.
Guo, Y.; Imahori, G.A.; Colon, L.A. *J. Chromatogr. A.* 1996, 744, 17–29.
Hawthorne, S.B.; *Anal. Chem.* 1990, 62, 633A–642A.
Hayes, J.D.; Malik, A. *Anal. Chem.* 2000, 72, 4090–4099.
Hayes, J.D.; Malik, A. *Anal. Chem.* 2001, 73, 987–996.
Hayes, J.D.; Malik, A. *J. Chromatogr. B* 1997, 695, 3–13.
Hirata, Y.; Pawliszyn, J. *J. Microcolumn Sep.* 1994, 6, 443–447.
In, M.; Gerardin, C.; Lambard, J.; Sanchez, C. *J. Sol. gel. Sci. Technol.*, 1995, 5, 101–114.
Iwamoto, T.; Mackenzie, J.D. *J. Sol–gel Sci. Technol.* 1995, 4, 141–150.
Janak, K.; Horka, M.; Krejci, M. *J. Microcol. Sep.* 1991, 3, 115–120.
Jiang, Z.–.; Zuo, Y.–. *Anal. Chem.* 2001, 73, 686–688.
Jinno, K.; Muramatsu, T.; Saito, Y.; Kiso, Y.; Magdic, S.; Pawliszyn J. *J. Chromatogr. A.* 1996, 754, 137–144.
Jones, S.A.; Wong, S.; Burlitch, J.M.; Viswanathan, S.; Kohlstedt, D.L. *Chem. Mater.* 1997, 9, 2567–2576.
Kataoka, H.; Lord, H.L.; Pawliszyn, J. *J. Chromatogr. B* 1999, 731, 353–359.
Kataoka, H.; Narimatsu, S.; Lord, H.; Pawliszyn, J. *Anal. Chem.* 1999, 71, 4237–4244.
Kataoka, H.; Pawliszyn, J. *Chromatographia* 1999, 50, 532–538.
Wang, D.–X.; Chong, S.–L; Malik, A. *Anal. Chem.* 1997, 69, 4566–4576.
Aichholz, Reiner, Preparation of Glass Capillary Columns . . . Journal of High Resolution Chromatography, vol. 13, pp. 71–73 (1990).
Alltech, Chromatography Catalog, pp. 172 (1997).
Algelt, Klaus H. et al., Chromatography on Petroleum Analysis, (1979), Marcel Dekker, New Yourk and Basel, pp. 1–119.
Belardi, Robert P. et al., The Application of Chemically Modified Fused Silica . . . , 24, pp. 179–191, (1989).
Berezkin, Victor G.; Drugov, Yuri S., Gas Chromatography in Air Pollution Analysis, (1991) Elsevier, pp. 165–207.
Berezkin, Victor G. et al., Capillary Columns with Several Layers . . . , vol. 47, pp. 600–604, (1992).
Blau, Karl; Halket, John M. Eds., Handbook of Derivatives for Chromatography, 2nd ed. (1993), John Wiley & Sons, pp. 1–31.
Bloomberg, L., Modification of Glass Capillary Columns . . . , Journal of HRC & CC, vol. 3, pp. 527, (1980).
Brinker, C. Jeffrey et al., Sol–Gel Science, Academic Press, (1990), pp. 97–233.
Brown, Phyllis R. et al., The Separation and the Characterization of Long Chain . . . , Critical Reviews in Analytical Chemistry, vol. 21, pp. 193–208, (1989).
Clement, Ray E., Gas Chromatography, Biochemical, Biomedical, and Clinical Applicants, (1990), Wiley, pp. 182–215.
Collinson, Maryanne M., et al., Sol–Gels and Electrochemistry, Analytical Chemistry, vol. 72, pp. 702A–709A, (2000).
Coulibaly, Kelegoun, et al., An Overview of Solid–Phase Extraction . . . , Food Rev. Int., vol. 12, pp. 131–151, (1996).
EPA Method 604, Methods for Organic Analysis . . . , Environmental Protection Agency, pp. 58–66, (1984).
Ettre, L. S., Performance of Open Tubular Columns . . . , Chromatographia, vol. 18, pp. 477–488, (1984).
Ettre, Leslie S., et al., Basic Relationships of Gas Chromatography, (1994), Advanstar, pp. 1–34.
Ferioli, V., et al., High–Performance Liquid Chromatography . . . , Chromatographia, vol. 14, pp. 61–65, (1995).
Fielding, M., et al. Disinfection By–products in Drinking Water, Current Issues, Royal Society of Chemistry (1999), pp. 1–9 & 46–53.
WHO Guidelines for Drinking–Water Quality, 2nd ed., WHO (World Health Organization), Geneva, (1993), pp. 1–16.
Hamlet, Christine, et al., Novel Sol–Gel Dendrimer Coatings . . . Mar. 2003 1 page.

Hartmann, H., et al., Trace Determination of Pesticides..., Fresenius Environmental Bulletin, vol. 7, pp. 96–103, (1998).

Haruvy, Y., et al., Sol–Gel Replication of Microoptical Elements and Arrays, Chem. Mater, vol. 9, pp. 2604–2615, (1997).

Hayes, J.D., et al, HPCE–Final Program, pp. 80–81, (1997).

Hayes, James D.; Malik, Abdul, Sol–Gel Monolithic Columns..., Analytical Chemistry, vol. 72, pp. 4090–4099, (2000).

Janak, K., et al., Static Coating of Capillary Columns..., Journal of HRC & CC, vol. 8, pp. 843–847, (1985).

Kataoka, Hiroyuki, et al., Simple and Rapid Determination of Amphetamine..., Journal of Anayltical Toxicology, vol. 24, pp. 257–265, (2000).

Koivusalmi, Eija, et al., Quantitative RP–HPLC Determination..., Analytical Chemistry, vol. 71, pp. 86–91, (1999).

Nawrocki, J., Silica Surface Controversies..., Chromatographia, vol. 31, pp. 177–205, (1991).

Lee, M.L., et al, Fused Silica Capillary Column Technology for Gas Chromatography, Journal of Chromatographic Science, vol. 22, pp. 136–142. (1984).

Lopez–Avila, Viorica, et al., Evaluation of Soxtec Extraction..., Journal of AOAC International, vol. 76, pp. 864–880, (1993).

MacKenzie, J.D., Hybrid Organic–Inorganic Materials, American Chemistry Society, pp. 227–236, (1995).

Majors, Ronald E., Liquid Extraction Techniques for Sample Preparation, LC*GC International, vol. 10, pp. 93–101, (1997).

Minnich, Marti M., et al., Extraction Methods for Recovery..., Journal of AOAC International, vol. 79, pp. 1198–1204, (1996).

Mukherjee, Shyama P., Supercritical Drying in Structural and Microstructural Evolution of Gels; A Critical Review, pp. 747–759, (1988).

Oesterhelt, G., et al., Analyse von Hydroxypivalaldehyd..., Fresenuis Z. Anal. Chem., vol. 321, pp. 553–555, (1985).

Palkar, V. R., Sol–Gel Derived Nonostructured..., Nano-Structured Materials, vol. 11, pp. 369–374, (1999).

Pawliszyn, Janusz, Theory of Solid–Phase Microextraction, Journal of Chromatographic Science, vol. 38, pp. 270–278, (1999).

Reighard, Tricia S., et al., Bridging the Gap Between Supercritical..., Critical Rev. in Analytical Chem., vol. 26, pp. 61–99, (1996).

Rotzsche, Harald, Stationary Phases in Gas Chromatography, Journal of Chromatography Library, vol. 48, Elsevier, (1991), pp. 142–159.

Scheppers Wercinski, Sue Ann, Solid Phase Microextraction: A Practical Guide, Marcel Dekker, Inc., (1999), pp. 1–27.

Schomburg, G., et al., Alkylpolysiloxane Galss Capillary Columns..., Chromatographia, vol. 12, pp. 651–660, (1979).

Shende, Chetan, et al., Sol–Gel Poly(ethylene gylcol) Stationary Phase..., Analytical Chemistry, vol. 75, pp. 3518–3530, (2003).

Stark, F. O., et al., The Interactions between Trialkylsilanes and E–Glass..., The Journal of Physical Chemistry, vol. 72, pp. 2750–2754, (1968).

Furton, Kenneth, et al., The Use of Solid–Phase..., Journal of Chromatographic Science, vol. 38, pp. 297–306, (2000).

Van Der Vlis, E., et al., Combined Liquid–liquid Electroextraction..., Journal of Chromatography A, pp. 333–341, (1994).

Vorotilov, K.A., et al., Ormosil Films: Properties and Microelectronic Applications, Journal of Sol–Gel Sci. and Tech. vol. 8, pp. 581–584, (1997).

Wang, Dongxin, Sol–Gel Chemistry—Mediated Novel Appraoch to column Technology for High–Resolution Capillary Gas Chromatography, (2000), pp. i–xix.

Wang, Dongxin, et al., Preparation and GC Performance of col–Gel Technology–Based Open Tubular Columns., pp. 505–513, (1996).

Wang, Zhenyu, et al., High–Performance Polyethylene..., Journal of Chromatography, vol. 893, pp. 157–168, (2000).

Welsch, Thomas, et al., The Thermal Immobilization of Hydroxy–Terminated Silicon..., Journal of High Resolution Chromatography, vol. 14, pp. 153–159, (1991).

Westwood, S.A., Supercritical Fluid Extraction and its Use on Chromatographic Sample Preparation, CRC Press, (1993), pp. 1–39.

Wilked, G.L., et al., "Creamers": Hybid Materials Incoporating..., Polymer Preprints, vol. 26, pp. 300–302, (1985).

Woolley, C.L., et al., Deactivation of Fused–Silica..., Journal of Chromatography, vol. 367, pp. 9–22, (1986).

Wu, Jingcun, et al., Polypyrrole–Coated Capillary In–Tube..., J. Microcolumn Separations, vol. 12, pp. 255–266, (2000).

Wu, Jingcun, et al., Polypurrole–Coated Capillary..., Analytical Chemistry, vol. 73, pp. 55–63, (2001).

Yakabe, Yoshikuni, et al., Immobilization method for polyethylene..., Journal of Chromatography, vol. 558, pp. 323–327, (1991).

Zapf, Andreas, et al., GC Analysis of Organic Acids..., Journal of High Resolution Chromatography, vol. 22, pp. 83–88, (1999).

Zeng, Zhaorui, et al., Solid Phase Microextraction Using Fused–Silica..., Analytical Chemistry, vol. 73, pp. 2429–2436, (2001).

Zhang, J., et al., Development of the Peronsal Aldehydes..., Environmental Science & Technology, vol. 34, pp. 2601–2607, (2000).

Zhang, Zhouyao, et al., Solid–Phase Microextraction, Analytical Chemistry, vol. 66, pp. 844A–853A, (1994).

* cited by examiner

SAMPLE PRECONCENTRATION TUBES WITH SOL-GEL SURFACE COATINGS AND/OR SOL-GEL MONOLITHIC BEDS

CROSS-REFERENCE SECTION

This application claims the benefit of priority under 35 U.S.C. Section 119(e) of U.S. Provisional Patent Application No. 60/242,534, filed Oct. 23, 2000, which is incorporated herein by reference.

BACKGROUND OF THE INVENTION

1. Field of the Invention

The present invention relates to methods of analytical sample preparation for instrumental analysis. More specifically, the present invention relates to a capillary microextraction technique for preconcentrating trace analytes.

2. Description of Related Art

Sample preparation is an important step in chemical analysis, especially when dealing with traces of target analytes dispersed in complex matrices. Such matrices are commonplace in samples from environmental, petrochemical, and biological origins. Samples of this nature are not generally suitable for direct introduction into analytical instruments. Such incompatibility is related to two factors. First, the complex matrices may have a detrimental effect on the performance of the analytical system or they may interfere with the analysis of the target analytes. Second, the concentration of the target analytes in the sample may be so low that it goes beyond the detection limit of the analytical instrument. In both cases sample preparation is necessary to make the sample compatible with analytical instrumentation. This is achieved through sample clean-up and sample preconcentration. Sample derivatization is also sometimes necessary to facilitate analysis and detection of target compounds.

Sample preparation in chemical analysis often involves various extraction techniques to isolate and preconcentrate target compounds from complex matrices in which they exist in trace concentrations. Conventional extraction techniques (e.g., liquid—liquid extraction (Majors, R. E. *LC*GC. Int.* 1997, 10, 93–101), Soxhlet extraction (Lopez-Avila, V.; Bauer, K.; Milanes, J.; Beckert W. F. *J. AOAC Int.* 1993, 76, 864 880), etc. frequently used for this purpose are often time-consuming and involve the use of large volumes of hazardous organic solvents.

To address environmental and health concerns associated with the use of large volumes of organic solvents and to reduce sample preparation time, newer extraction techniques have been developed that use either reduced amounts of organic solutes such as solid-phase extraction (SPE), (Coulibaly, K; Jeon I. J. *Food Rev. Int.* 1996, 12, 131–151), accelerated solvent extraction (ASE) (Richter, B. E.; Jones, B. A.; Ezzel, J. L.; Porter N. L.; Abdalovic N.; Pohl, C. *Anal. Chem.* 1996, 1033–1039), microwave-assisted solvent extraction (MASE) (Zlotorzynski, A. *Crit. Rev. Anal. Chem.* 1995, 25, 43–76), etc. Another approach to address these problems was to develop sample preparation techniques using alternative, less hazardous extraction media, such as supercritical fluid extraction (SFE) (Hawthorne, S. B.; *Anal. Chem.* 1990, 62, 633A–642A). However, the extraction technique which is most fascinating from the environmental and occupational health and safety points of view is solid-phase microextraction (SPME) developed by Pawliszyn and coworkers (Berladi, R. P.; Pawliszyn, J. *Water Pollut. Res. J. Can.* 1989, 24, 179–91; Arthur, C. L.; Pawliszyn, J. *Anal. Chem.* 1990, 62, 2145). SPME completely eliminates the use of organic solvents for the extraction of analytes from a wide range of matrices. Another important feature of SPME is that, unlike conventional extraction techniques, it does not require exhaustive extraction-establishment of equilibria between the sample matrix and the stationary phase coating is sufficient to obtain quantitative extraction data. For most samples, the equilibration time is less than 30 minutes, which places SPME among the fastest extraction techniques.

In SPME, the outer surface of a solid fused silica fiber (approximately 1 cm at one end) is coated with a selective stationary phase. Thermally stable polymeric materials that allow fast solute diffusion are commonly used as stationary phases. The extraction operation is carried out by simply dipping the coated fiber into the sample matrix and allowing time for the partition equilibrium to be established. The sensitivity of the method, is mostly governed by the partition coefficient of an analyte between the coating and the matrix. Extraction selectivity can be achieved by using appropriate types of stationary phases that exhibit high affinity toward the target analytes.

In its traditional format, SPME has a number of drawbacks. First, since the stationary phase coating is applied to the outer surface of the fiber, it is more vulnerable to mechanical damage. Second, traditional methods for the preparation of coatings fail to provide adequate thermal and solvent stability to the thick stationary phase (several tens of micrometers in thickness) coatings that are needed in SPME. This is due to the lack of chemical bonding between the coatings and the substrate to which they are applied.

In recent years, the extraction of analytes by GC stationary phase coatings on the capillary inner surface has received considerable attention. The introduction of in-tube SPME had the primary purpose of coupling SPME to high-performance liquid chromatography (HPLC) for automated applications. The in-tube SPME method uses a flow-through process where a coated capillary is employed for the direct extraction of the analytes from the aqueous sample. The extraction process involves agitation by sample flow in and out of the extraction capillary. Successful coupling of in-tube SPME with HPLC, as well as HPLC-MS, has been achieved for the specification of organoarsenic compounds, (Wu, J.; Mester, Z.; Pawliszyn, J. *Anal. Chem.* 1999, 71, 4237–4244) and determination of rantidine, (Kataoka, H.; Lord, H. L.; Pawliszyn, J. *J. Chromatogr. B* 1999, 731, 353–359) β-blockers, (Kataoka, H.; Narimatsu, S.; Lord, H.; Pawliszyn, J. *Anal. Chem.* 1999, 71, 4237–4244) carbamate pesticides, (Gou, Y.; Pawliszyn, J. *Anal. Chem.* 2000, 72 2774–2779; Gou, Y.; Eisert, R.; Pawliszyn, J. *J. Chromatogr. A* 2000, 873, 137–147; Gou, Y.; Tragas, C.; Lord, H.; Pawliszyn, J. *J. Micro Sep.* 2000, 12, 125–134) and aromatic compounds (Wu, J.; Pawliszyn, J. *J. Chromatogr. A* 2001, 909, 37–52).

In spite of rapid on-going developments, especially in the areas of in-tube SPME applications, a number of fundamental problems remain to be solved. First, GC capillaries that are used for in-tube SPME typically have thin coatings that significantly limit the sample capacity (and hence sensitivity) of the technique. Conventional static coating techniques (Bouche, J.; Verzele, M. *J. Gas Chromatogr.* 1968, 6, 501–505; Janak, K.; Kahle, V.; Tesarik, K.; Horka, M. *J. High Resolut. Chromatogr./Chromatogr. Commun.* 1985, 8, 843–847; Sumpter, S. R.; Woolley, C. L.; Hunag, E. C.; Markides, K. E.; Lee, M. L. *J. Chromatogr.* 1990, 517, 503–519) used to prepare stationary phase coatings in GC columns are designed primarily for creating thin (submicrometer thickness) coatings. Thus, developing an alternative technique to provide higher coating thickness suitable for in-tube SPME applications is very important. Second, usually the stationary phase coatings used in GC capillaries are not chemically bonded to the capillary surface. In conventional approaches, these relatively thin coatings are immobilized on the capillary inner surface though free-radical cross-linking reactions. (Wright, B. W.; Peaden, P. A.; Lee, M. L.; Stark, T. J. *J. Chromatogr.* 1982, 248, 17–34; Blomberg, L. G. *J. Microcol. Sep.* 1990, 2, 62–68) Immobilization of thicker coatings (especially the polar ones) is difficult to achieve. (Janak, K.; Horka, M.; Krejci, J. *J. Microcol. Sep.* 1991, 3, 115–120; Berezkin, V. G.; Shiryaeva, V. E.; Popova, T. P. *Zh. Analit. Khim.* 1992, 47, 825–831) Third, because of the absence of direct chemical bonding between the stationary phase coating and the GC capillary inner walls, the thermal and solvent stabilities of such coatings are typically poor or moderate. When such extraction devices are coupled to GC, reduced thermal stability of thick GC coatings leads to incomplete sample desorption and sample carryover problems. (Buchholz, K. D.; Pawlyszyn, J. *Anal. Chem.* 1994, 66, 160–167; Zhang, Z.; Yang, M. J.; Pawliszyn, J. *Anal Chem.* 1994, 66, 844A–853A.; Potter, D. W.; Pawliszyn, J. *Environ. Sci. Technol.* 1994, 28, 298–305)

Low solvent stability of conventionally prepared thick stationary phase coatings present a significant obstacle to the hyphenation of in-tube SPME with liquid-phase separation techniques that employ organic or organo-aqueous mobile phase systems of the desorption of analytes. Solvent stability of the in-tube SPME coatings is, therefore, fundamentally important for further development of the technique. (Wu, J.; Pawliszyn, J. *Anal Chem.* 2001, 73, 55–63) Thus, these three problems need to be solved in order to exploit full analytical potential of in-tube SPME.

SUMMARY OF THE INVENTION

In accordance with the present invention, there is provided a method of preconcentrating trace analytes by extracting polar and non-polar analytes through a sol-gel coating and/or sol-gel monolithic bed. The present invention further provides a microextraction method including the steps of micro-extracting polar and non-polar analytes in a sol-gel coating and/or sol-gel monolithic bed, desorbing the analytes from the sol-gel and analyzing the extracted, desorbed analytes.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1A:
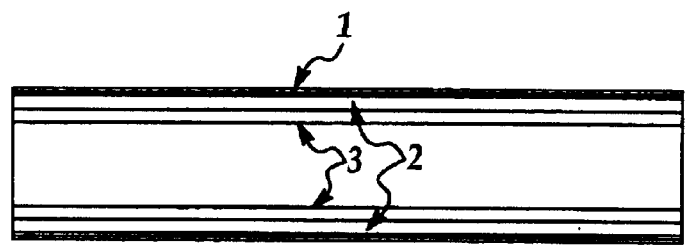
FIGS. 1A and B show an extraction tube made in accordance with the present invention.

Generally, the present invention provides a method and apparatus for preconcentrating trace analytes. Most generally, the method involves the step of extracting polar and non-polar analytes through a sol-gel coating or monolithic bed. The sol-gel has the formula:

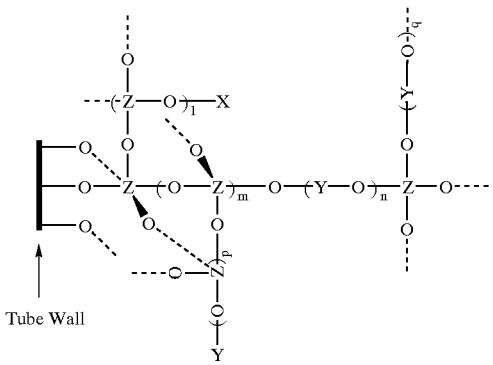

wherein,
- X=Residual of a deactivation reagent (e.g., polymethylhydrosiloxane (PMHS), hexamethyldisilazane (HMDS), etc.);
- Y=Sol-gel reaction residual of a sol-gel active organic molecule (e.g., hydroxy terminated molecules including polydimethylsiloxane (PDMS), polymethylphenylsiloxane (PMPS), polydimethyldiphenylsiloxane (PDMDPS), polyethylene glycol (PEG) and related polymers like Carbowax 20M, polyalkylene glycol such as Ucon, macrocyclic molecules like cyclodextrins, crown ethers, calixarenes, alkyl moieties like octadecyl, octyl, etc.
- Z=Sol-gel precursor-forming chemical element (e.g., Si, Al, Ti, Zr, etc.)
- l=An integer$\geq 0$;
- m=An integer$\geq 0$;
- n=An integer$\geq 0$;
- p=An integer$\geq 0$;
- q=An integer$\geq 0$;

and
  l, m, n, p, and q are not simultaneously zero.

Dotted lines indicate the continuation of the chemical structure with X, Y, Z, or Hudrogen (H) in space.

In order to achieve the desired sol-gels of the instant invention, certain reagents in a reagent system were preferred for the fabrication of the gels for the monolithic columns of the present invention. The reagent system included two sol-gel precursors, a deactivation reagent, one or more solvents and a catalyst. For the purposes of this invention, one of the sol-gel precursors contains a chromatographically active moiety selected from the group consisting of octadecyl, octyl, cyanopropyl, diol, biphenyl, phenyl, cyclodextrins, crown ethers and other moieties. Representative precursors include, but are not limited to: Tetramethoxysilane, 3-(N-styrylmethyl-2-aminoethylamino)-propyltrimethoxysilane hydrochloride, N-tetradecyidimethyl(3-trimethoxysilylpropyl)ammonium chloride, N(3-trimethoxysilylpropyl)-N-methyl-N,N-diallylammonium chloride, N-trimethoxysilylpropyltri-N-butylammonium bromide, N-trimethoxysilylpropyl-N,N,N-trimethylammonium chloride, Trimethoxysilylpropylthiouronium chloride, 3-[2-N-benzyaminoethylaminopropyl]trimethoxysilane hydrochloride, 1,4-Bis(hydroxydimethylsilyl)benzene, Bis(2-hydroxyethyl)-3-aminopropyltriethoxysilane, 1,4-bis(trimethoxysilylethyl)benzene, 2-Cyanoethyltrimethoxysilane, 2-Cyanoethyltriethoxysilane, (Cyanomethylphenethyl)trimethoxysilane, (Cyanomethylphenethyl)triethoxysilane, 3-Cyanopropyldimethylmethoxysilane, 3-Cyanopropyltriethoxysilane, 3-Cyanopropyltrimethoxysilane, n-Octadecyltrimethoxysilane, n-Octadecyldimethylmethoxysilane, Methyl-n-Octadecyldiethoxysilane, Methyl-n-Octadecyldimethoxysilane, n-Octadecyltriethoxysilane, n-Dodecyltriethoxysilane, n-Dodecyltrimethoxysilane, n-Octyltriethyoxysilane, n-Octyltrimethoxysilane, n-Ocyidiisobutylmethoxysilane, n-Octylmethyldimethoxysilane, n-Hexyltriethoxysilane, n-isobutyltriethoxysilane, n-Propyltrimethoxysilane, Phenethyltrimethoxysilane, N-Phenylaminopropyltrimethoxysilane, Styrylethyltrimethoxysilane, 3-(2,2,6,6-tetramethylpiperidine-4-oxy)-propyltriethoxysilane, N-(3-triethoxysilylpropyl)acetyl-glycinamide, (3,3,3-trifluoropropyl)trimethoxysilane, and (3,3,3-trifluoropropyl)methyidimethoxysilane.

A second sol-gel precursor, N-Octadecyldimethyl[3-(trimethoxysilyl)propyl]ammonium chloride, was found to be desirable since it possessed an octadecyl moiety that allowed for chromatographic interactions of analytes with the monolithic stationary phase. Additionally, this reagent served to yield a positively charged surface thereby providing the relatively high reversed electroosmotic flow necessary in capillary electrochromatography. However, it is considered within the scope to use any other reagent as known to one of ordinary skill in the art that would contain the octadecyl moiety for the purposes already set forth.

The deactivation reagent, Phenyldimethylsilane, and the catalyst, Trifluoroacetic acid, were selected for the preparation of the columns of the instant invention, however, any deactivation reagent and/or catalyst as known to those of ordinary skill in the art may be used.

More specifically, the present invention provides the method of preconcentrating both polar and non-polar analytes by feeding a sample through a sol-gel coated inner-surface of a tube or through a sol-gel monolithic bed and extracting analytes from the sample utilizing the sol-gel coating.

FIGS. 1A and B show extraction tubes made in accordance with the present invention. FIG. 1A (FIG. 1B discussed below) shows a tube wall 2, preferably made from fused silica but can be made from other materials known in the art, having an inner sol-gel containing 3. A protective outer coating 1 is dispersed over the outer surface of the tube 2, and defines the outer surface of the extraction tube device. The protective polymeric outer coating is most commonly made out of polyimide. The protective coating comes as a standard feature of the commercially available fused silica capillary. The protective coating is applied to the outer surface during capillary manufacturing process. It is not part of the present invention.

Figure 1B:
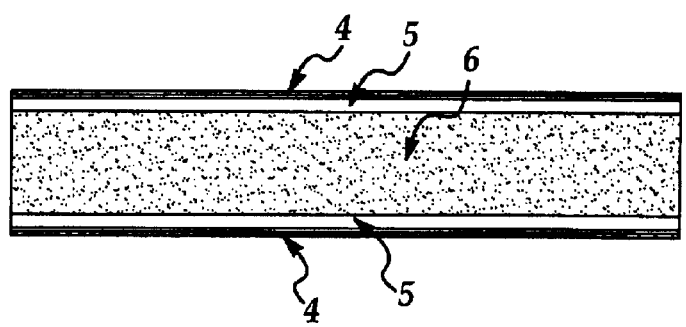
Figure 18:
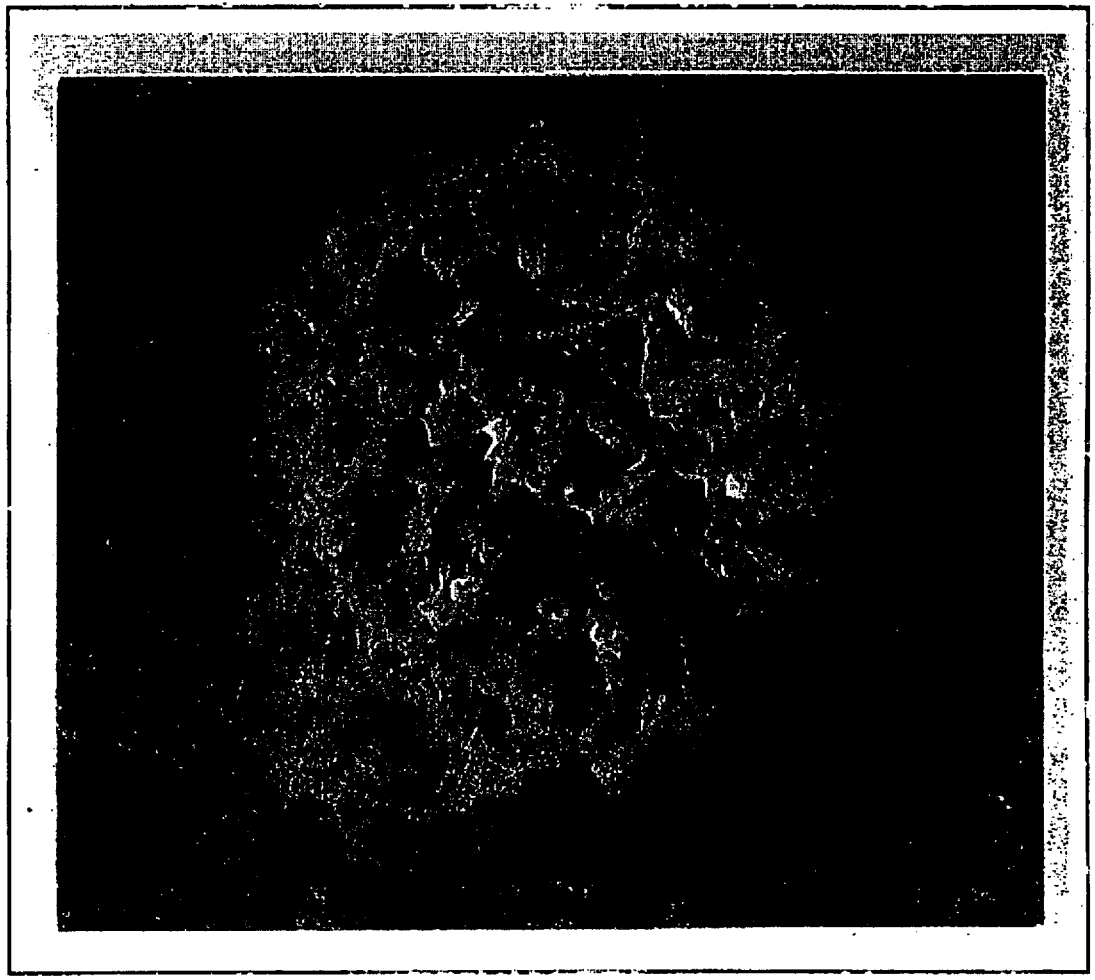
FIG. 18 is a scanning electron micrograph of a cross section of a monolithic bed made in accordance with the present invention.

FIG. 1B shows an alternative extraction tube device. A tube wall 5 contains a sol-gel monolithic bed 6 there within. The tube wall 5 includes a protective coating 4 disposed over its outer surface. FIG. 18 is a scanning electron micrograph cross section of a fused silica capillary tube containing the monolithic sol-gel bed there within. The matrix structure of the bed is shown.

Figure 9:
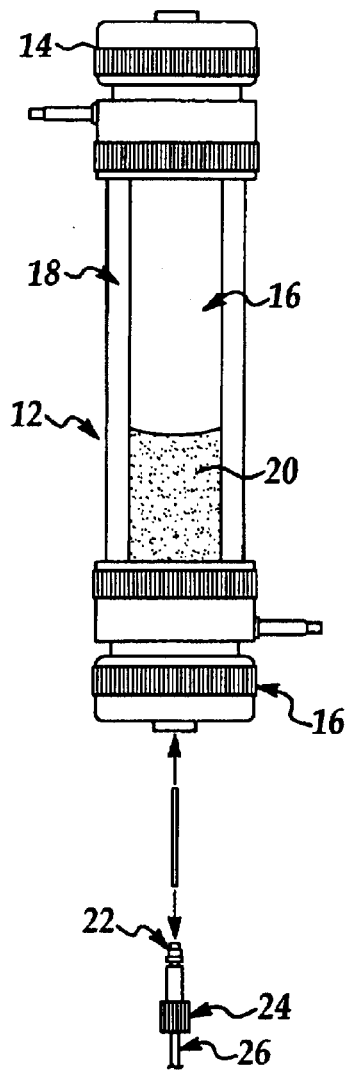
FIG. 9 is a schematic side view, partially broken away, of a gravity-fed extraction system for capillary microextraction made in accordance with the present invention.

FIG. 9 is an example of capillary microextraction apparatus made in accordance with the present invention. FIG. 9 shows a glass sample reservoir, generally indicated at 10, for use in capillary microextraction in accordance with the present invention. The apparatus consists of a column generally shown at 12 and top and bottom screw caps 14 and 16.

The column 12 includes an internal deactivated glass column 16 surrounded by an acrylic jacket 18. As shown in cross section in FIG. 9, the gravity feed microextraction system is shown to include the acrylic jacket 18 surrounding the sample containing the analytes of interest 20 disposed within the deactivated glass column 16. The lower screw caps 16 is connected through a polypropylene ferrule 22 and a connecting plastic nut 24 to PEEK tubing 26.

Figure 2:
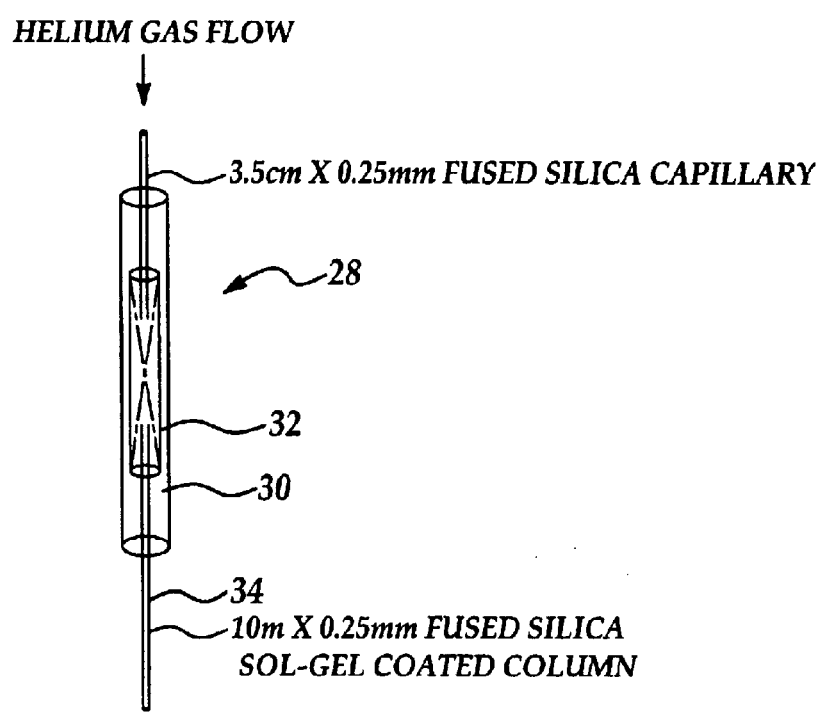
FIG. 2 shows a schematic perspective representation of a gas chromatograph injector port and a capillary tube made in accordance with the present invention connected with a gas chromatographic column.
Figure 3:
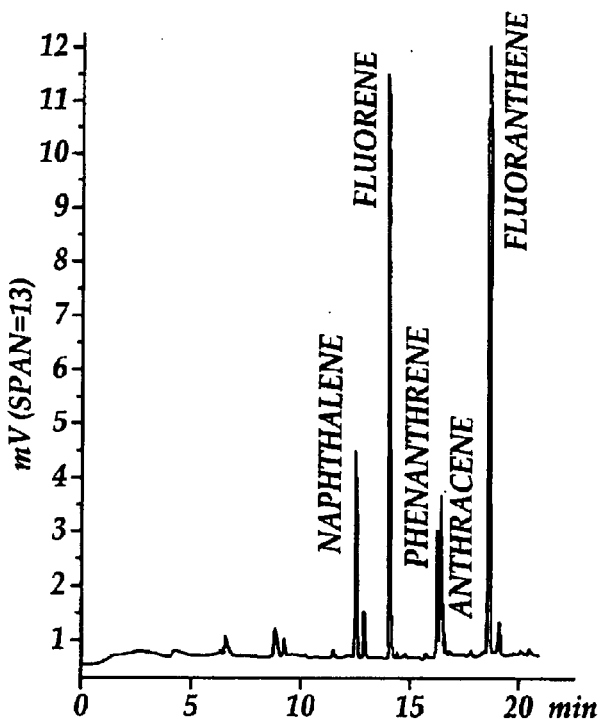
FIG. 3 shows a gas chromatographic analysis of PAHs extracted from water in accordance with the present invention.
Figure 4:
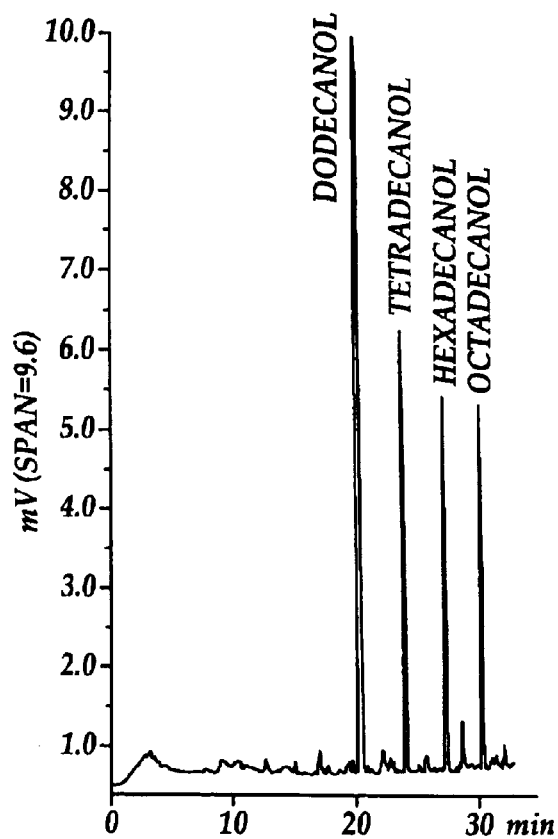
FIG. 4 is a gas chromatographic analysis of alcohols using the sol-gel capillary microextraction of the present invention.
Figure 5:
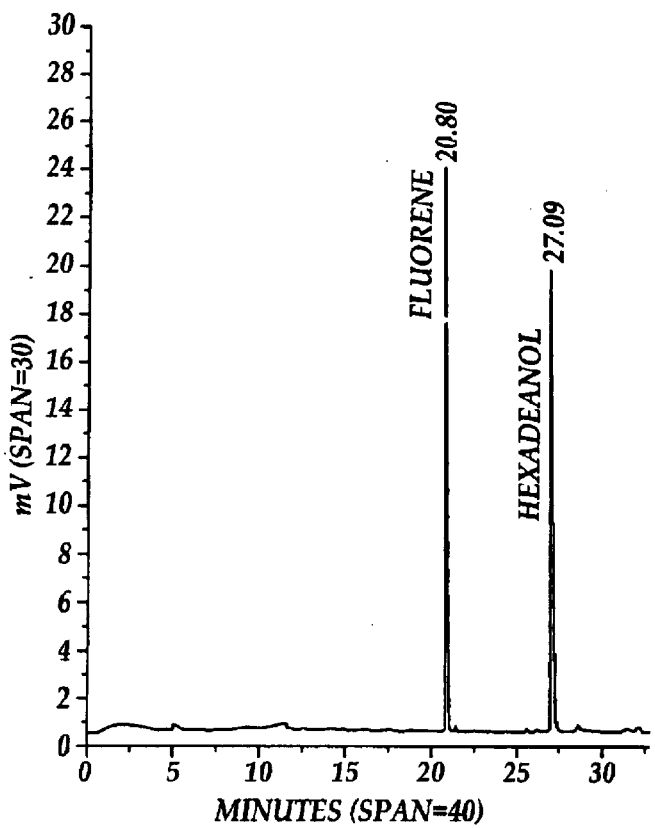
FIG. 5 is a gas chromatographic analysis showing microextraction of polar and non-polar analytes from water.
Figure 6:
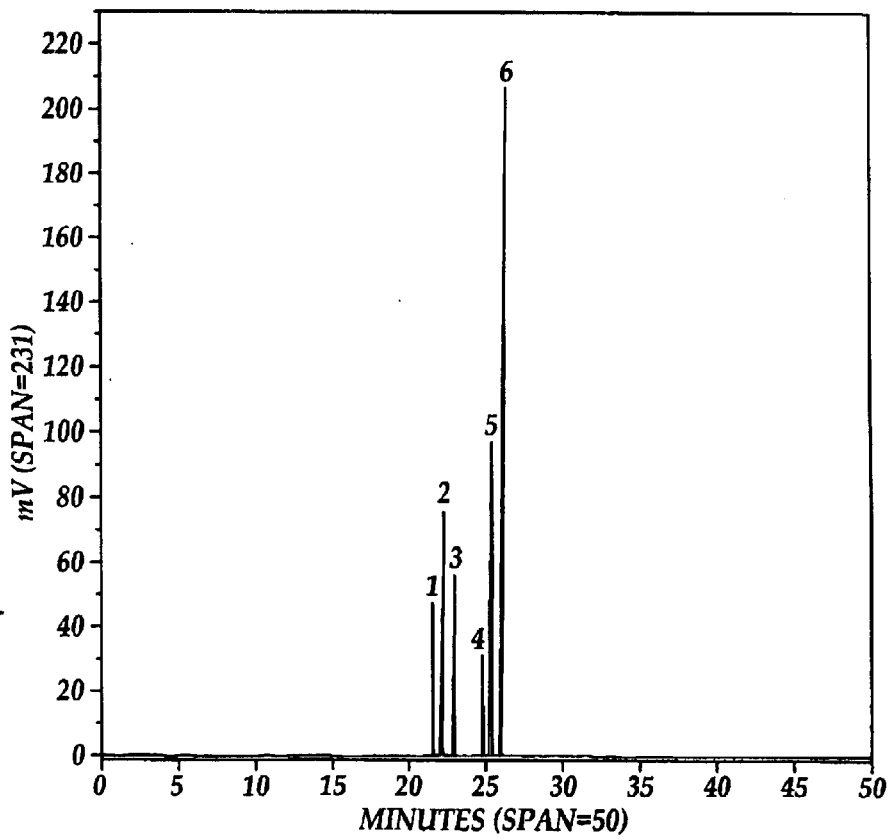
FIG. 6 is a gas chromatographic analysis showing separation of ketones using the capillary microextraction technology of the present invention.

FIG. 2 illustrates introduction of an extracted sample into a gas chromatograph. The device shown generally at 28 includes a glass insert 30 surrounding a fused silica two-way capillary connector 32. Retained by the connector is a fused silica sol-gel coated column 34 made by the process described below.

The preparation of the sol-gel coating on the inner surface of a tube includes the steps of providing the tube structure, a sol-gel solution comprising a sol-gel precursor, an organic material with at least one sol-gel active functional group, a sol-gel catalyst, a deactivation agent, and a solvent system as defined above. The sol-gel solution is then reacted with the inner surface of the tube under controlled conditions to produce a surface bonded sol-gel coating on that portion of the tube. The solution is then removed from the tube under pressure of an inert gas and is heated under controlled conditions to cause the deactivation reagent to react with the surface bonded sol-gel coating to deactivate and to condition the sol-gel coated portion of the tube structure. Preferably, the sol-gel precursor includes an alkoxy compound. The organic material includes a monomeric or polymeric material that at least one sol-gel active functional group. The sol-gel catalyst is taken from the group consisting of an acid, a base, a fluoride compound. The deactivation reagent includes a material reactive to polar functional groups, such as hydroxyl groups, bonded to the sol-gel precursor-forming element in the coating or the tube structure.

The monolithic bed is made by first filling a tube with the sol-gel solution. By this single step filling, the sol-gel is produced which forms a porous matrix to be used for separation purposes. The matrix includes a positively charged surface within the matrix. That is, the microstructure of the sol-gel monolithic separation bed constitutes an infinite number of pathways through the porous matrix. The charges on the surface of the matrix generate an electroosmotic flow. Since the surface is positively charged, a reverse flow is created which is much easier to control than that of the prior art native silica surfaces. Such a monolithic bed provides a particle free sol-gel solution which forms the preparation bed.

The sol-gel coating and monolithic bed can occur through numerous methodologies, alternative to the above. In a further coating method, the surface is coated with a sol-gel solution than includes a sol-gel precursor that includes, but is not limited to, alkoxysaline precursors such as methyltrimethoxysilane, traalkoxysilanes, and any other similar precursors known to those skilled in the art. Additionally, the sol solution contains a coating polymer that includes, but is not limited to hydroxy terminated polydimethylsiloxane. Finally, common to the preparation as discussed above, the solution contains a deactivation reagent and a sol-gel catalyst. The deactivation reagent can be, but is not limited to, PMHS and any other similar substance known to those skilled in the art. As for the sol-gel catalyst, an acid catalyst such as trifluoroacetic acid containing 5% water is preferred. Once the sol-gel solution is placed onto the surface of the material, conditioning occurs under various parameters known to those skilled in the art. Furthermore, there are two major sets of reactions that take place during sol-gel processing. There the hydrolysis of the precursor and the polycondensation of the hydrolyzed products and other sol-gel active moieties in the system.

As detailed in the experimental section below, specific formulations and methods are provided herein.

EXPERIMENTAL SECTION

Two series of experiments were conducted demonstrating the applicability and utility of the present invention. Each section discussed below demonstrates both the open tube and monolithic bed columns ability to separate polar and non-polar analytes, even during the same extraction. Likewise, each set of experiments demonstrates the ability of the present invention to separate trace analytes at what was prior though to be inconceivable trace amounts. Parts per quadrillion extractions were obtained utilizing the monolithic bed of the present invention.

Experimentation Series 1

Chemicals and materials. Fused silica capillary of 250 μm internal diameter (i.d.) was purchased form Polymicro Technologies (Phoenix, Ariz.). HPLC-grade methylene chloride and methanol were purchased form Fisher Scientific (Pittsburgh, Pa.). Trifluoroacetic acid (TFA) and polymethylhydrosiloxane (PHMS) were procured from Aldrich Chemical Co. (Milwaukee, Wis.). Methyltrimethoxysilane (MTMS) was obtained from United Chemical Co. (Bristol, Pa.). Highly pure deionized water (18 Ω) was prepared in-house from a Barnstead model 04741 Nanopure deionized water system (Barnstead/Thermodyne, Debuque, Iowa). Eppendorf micro centrifuge tubes (1.5 mL) were purchased from Brinkman Instruments (Westbury, N.Y.).

Equipment. Gas chromatographic experiments were carried out on a Shimadzu 17 GC system (Shimadzu Scientific, Baltimore, Md.) equipped with a split/splitless injector and a flame ionization detector (FID). A Barnstead model 04741 Nanopure deionized water system (Barnstead/Thermodyne, Debuque, Iowa) was used to prepare highly pure deionized water (18 Ω). A Microcentaur model APO 5760 centrifuge (Accurage Chemical and Scientific Corp., Westbury, N.Y.) was employed for necessary centrifugation of the sol-gel solution. A fisher model G-560 Vortex Genie 2 system (Fisher Scientific, Pittsburgh, Pa.) was used for thorough mixing of the sol solution ingredients while preparing the sol solutions. A home-made gas-pressure operated filling/purging device (J. D. Hayes, A. Malik, *Anal Chem.* 2000, 72, 4090–4099) was used for filing the fused silica capillary with the sol solution, as well as rinsing and purging with helium at various stages of column preparation.

Preparation of the sol-gel solution. For this, 0.1 g of the selected sol-gel-active polymer was dissolved in 100 μL of methylene chloride placed in a micro centrifuge tube (1.5 mL). PMHS (40 μL) and MTMS (100 μL) were added to this solution, and the contents of the centrifuge tube were thoroughly vortexed. Finally, 100 μL of TFA containing 5% water (sol-gel catalyst and source of water) was added to centrifuged for 4 min at 13,000 rpm (15,682 G) to separate out any precipitate that might have formed during the mixing process. The clear sol solution from the top part of the centrifuge tube was then transferred to a clean vial for further use.

Preparation of Coatings for Capillary Microextraction. The sol-gel solution was used to prepare open tubular GC columns following a general procedure described in an earlier publication (D.-X. Wang, S.-L. Chong, and A. Malik, *Anal. Chem.*, 1997, 69 (22), 4566–4576). Briefly, a hydrothermally treated fused silica capillary (10-m×250 μm i.d.) was filled with the sol-gel solution using a home-made filling/purging device (Hayes, J. D.; Malik, A. J. Chromatogr. B., 1997, 695, 3–13) under 100 psi helium pressure. The solution was allowed to stay inside the capillary for 15 min after which it was expelled from the capillary under the same helium pressure. Following this, the capillary was dried by purging it with helium for 30 min at room temperature. The capillary was then thermally conditioned under a continuous flow of helium: from 40° C. to 280° C. @ 1° C. min$^{-1}$, holding the column at the final temperature for five hours. Finally, the column was rinsed with methylene chloride and dried under helium purge. At this point, the column was ready for analytical use.

Preparation of Monolithic beds for Microextraction. The monolithic extraction beds were prepared following a recently developed procedure. (J. D. Hayes, A. Malik, *Anal. Chem.* 2000, 72, 4090–4099) Briefly, a fused silica capillary was filled with the sol solution and allowed to stay inside the capillary for an extended period (a few hours). During this time sol-gel reactions proceed inside the capillary and the sol solution transforms into a porous solid matrix. The capillary is then heated (from 30° C. to the final temperature which may vary depending on the monolith material using a program rate of @ 0.2° C. min$^{-1}$) with both ends sealed, holding it at the final temperature for two hours. After this, the monolithic capillary is rinsed with a series of appropriate solvents (e.g., methylene chloride, methanol and water). Finally, the monolith is thermally conditioned (e.g, at 300° C.) with continuous purge with an inert gas before use for extraction.

Result and Discussion

FIG. 9 shows the glass sample reservoir used for capillary microextraction. It was properly deactivated using a surface derivatizing reagent (e.g., hexamethyldisilazane, HMDS) before use. It is vertically clamped with the water sample inside it. The surface-coated capillary/monolithic capillary was connected to the lower end and the sample was allowed to flow through it for 30 minutes. After that the capillary was purged with helium at room temperature for up to 5 minutes. It was the placed inside the GC injector port, and connected with a GC column (also made by sol-gel technology) with the help of a press-fit fused silica connector (FIG. 2). The extracted sample was desorbed by using a fast temperature programming of the GC injector.

Figure 7:
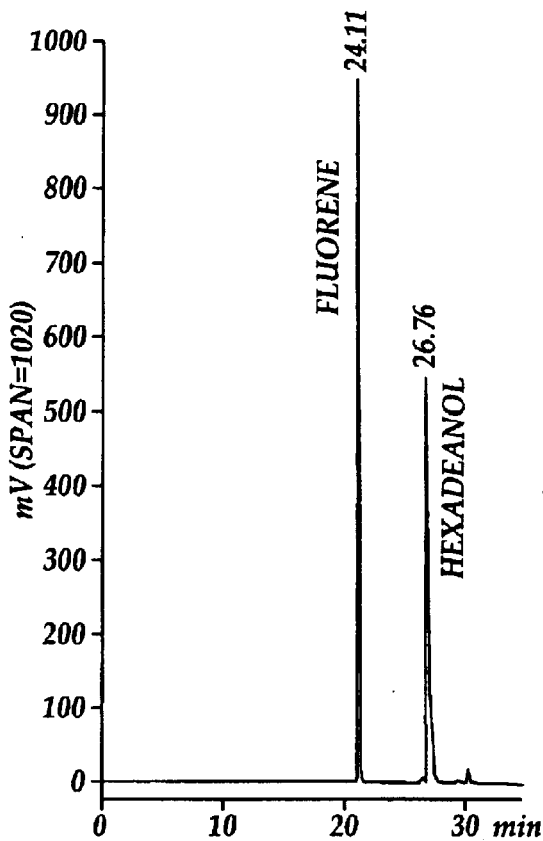
FIG. 7 is a gas chromatographic analysis showing the separation of fluorene from hexadecanol after capillary microextractions utilizing a sol-gel monolithic bed in accordance with the present invention.
Figure 8:
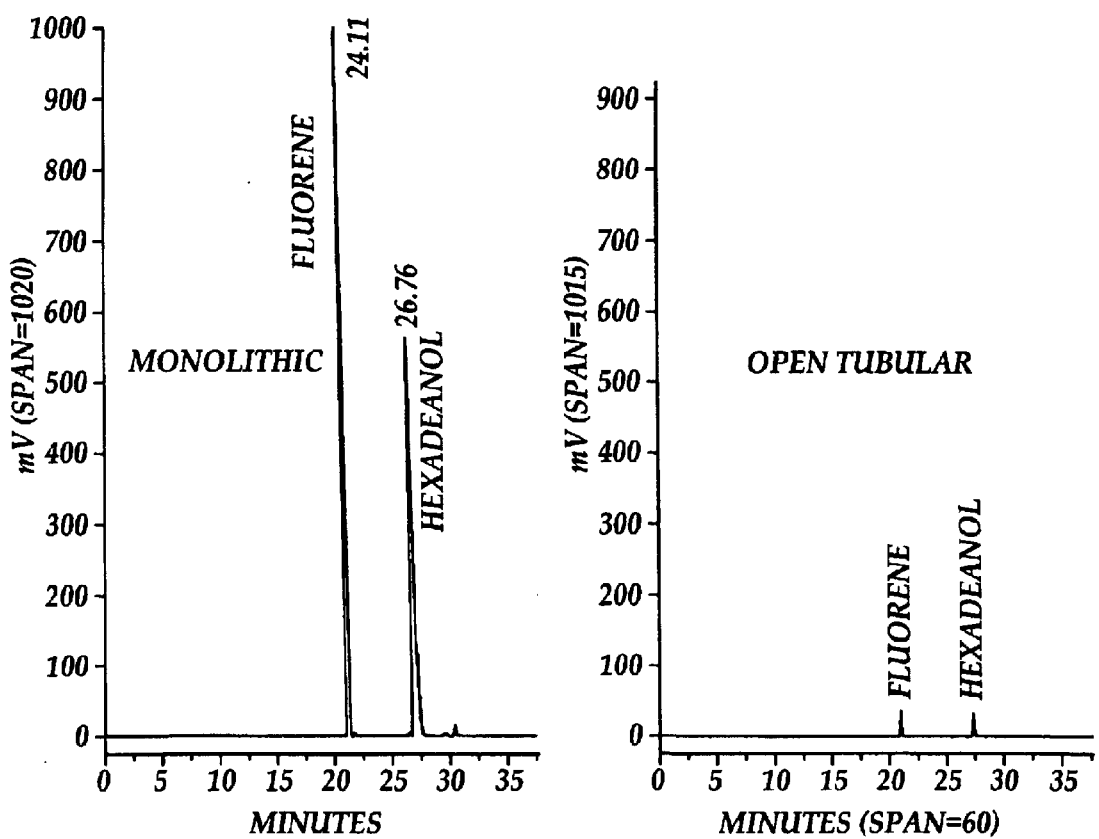
FIG. 8 is a comparison of gas chromatographic analyses showing the separation of fluorene from hexadecanol after capillary microextractions in accordance with the present invention utilizing a monolithic bed versus an open tubular construction.

FIGS. 3–6 illustrate the performance of microextraction capillaries with surface-bonded sol-gel coatings. The extraction conditions for the capillaries involve the use of a sol-gel PDMS coated capillary (35 mm by 250 micromolers I.D.) The extraction took a total of 30 minutes. The capillary was placed inside a GC injector port and connected with a GC column, which was a sol-gel PDMS column (10 meters by 250 micrometers I.D.) at 30° C. for 5 minutes and then it remained at 6° C. per minute thereafter. As can be seen from these figures, sol-gel coated microextraction capillaries can extract both polar and non-polar analytes from aqueous environment. Moreover, these coatings can extract the both types of analytes simultaneously. The same is true for sol-gel microextraction capillaries with monolithic beds as illustrated in FIGS. 7–8. The capillary microextraction, results of which are shown on FIG. 7, involve a sol-gel ODS monolithic bed (35 mm by 50 micrometers I.D. with one PPM). The extraction time was 30 minutes with desorption at 300° C. The capillary was then placed inside the GC injector port and connected with the GC column wherein the GC column is a sol-gel PDMS column (10 meters by 250 micrometers I.D.) The GC conditions were at 30° C. for 5 minutes and the heat was increased at 6° C. per minute. As is evident from FIG. 8, sol-gel monolithic microextraction capillaries are characterized by sample capacities that are a few orders of magnitude higher than the open tubular counterparts which, in turn, have significantly higher sample capacity than conventional SPME.

Experimentation Series 2

Equipment. SPME-GC experiments were carried out on a Varian Model 3800 capillary GC system equipped with an FID and a Varian Model 1079 temperature programmable split-splitless injector. Simple modifications to the split/splitless injector were made such that an extraction capillary could be inserted completely inside the injection port. An in-house designed liquid sample reservoir (FIG. 9) was used to facilitate gravity-fed flow of the aqueous samples through the sol-gel microextraction capillary. A Microcentaur model APO 5760 microcentrifuge (Accurage Chemical and Scientific Corp., Westbury, N.Y.) was used for centrifugation (@13,000 RPM; 15,682 g) of sol solutions used of for the preparation of sol-gel coated capillaries. A Fisher model G560 Vorten Genie 2 system (Fisher Scientific, Pittsburgh, Pa.) was used for thorough mixing of various solutions. A homemade, gas pressure-operated capillary filling/purging device was used to purge the sol-gel extraction capillary with helium after performing the microextraction procedure. A Barnstead Model 04741 Nanopure deionized water system (Barnstead/Thermodyne, Dubuque, Iowa) was used to obtain 17.6 MΩ water. On-line data collection and processing were done using ChromPerfect for Windows (Version 3.5) computer software (Justice Laboratory Software, Mountain Views, Calif.).

Chemicals and materials. Fused silica capillary (250 µm i.d.) with protective polyimide coating was purchased form Polymicro Technologies Inc. (Phoenix, Ariz.). Naphthalene and HPLC-grade solvents (tetrahydrofuran (THF), methylene chloride, and methanol) were purchased from Fisher Scientific (Pittsburgh, Pa.). The ketone, 4'-phenylacetophenone, was obtained from Eastman Organic Chemicals (Rochester, N.Y.). Hexamethyidisilazane (HMDS), poly(methylhydroxiloxane) (PMHS), trifluoroacetic acid (FTA), ketones (valerophenone, hexanophenone, heptonophenone, decanophenone, anthraquinone), aldehydes (benzaldehyde, nonylaldehyde, tolualdehyde, n-decylaldehyde, undecylic aldehyde), PAHs (acenaphthylene, flourene, phenanthrene, fluoranthene), and phenols (2,6-dimethylphenol, 2,5-dimethylphenol, 2,3-dimethylphenol, 3,4-dimethylphenol) were purchased from Aldrich (Milwaukee, Wis.). Hydroxy-terminated poly (dimethylsiloxane) (PDMS) and methylthrimethoxysilane (MTMS) were purchased form United Chemical Technologies, Inc. (Bristol, Pa.). Trimethoxysilane-derivatized polyethylene glycols (M-SIL-5000 and SIL-3400) were obtained from Shearwater Polymers (Huntsville, Ala.).

Preparation of Aqueous Standard Solutions for Capillary Microextraction. Stock solutions of polycyclic aromatic hydrocarbons (PAHs) (naphthalene, acenaphthylene containing 20% acenaphthene, fluorene, phenanthrene, fluoranthene) and ketones (4'-phenylacetophenone and anthraquinone) were prepared by dissolving 10 mg of each compound in 10 mL of THF in a 10 mL volumetric flask at room temperature. A 25-µL portion of this standard solution was diluted with deionized water to give a total volume of 25 mL that corresponded to a 1 ppm PAH aqueous solution. Preparation of 100 ppb and 1 ppb PAH solutions were accomplished by further dilution of this stock solution with deionized water. Stock solutions of ketones (valerophenone, hexanophenone, heptonophenone, decanophenone) or aldehydes (benzaldehyde, nonylaldehyde, tolualdehyde, n-decylaldehyde, undecyclic aldehyde) were also prepared using THF as the initial organic solvent. Stock solutions of dimethylphenol (DMP) isomers (2,6-dimethylphenol, 2,5-dimethylphenol, 2,3-dimethylphenol, 3,4-dimethylphenol) were prepared in an analogous way-using methanol as the initial organic solvent.

Prior to extraction, all glassware was deactivated. The glassware was cleaned using Sparkleen detergent and rinsed with generous amounts of deionized water, and dried at 150° C. for two hours. The inner surface of the dried glassware was then treated with 5% v/v solution of HMDS in methylene chloride, followed by placing of the glassware in an oven at 250° C. overnight. The glassware were then rinsed sequentially with methylene chloride and methanol, and further dried in the oven at 100° C. for 1 hour. Before use, they were rinsed with generous amounts of deionized water and dried at room temperature in a flow of helium.

Figure 10:
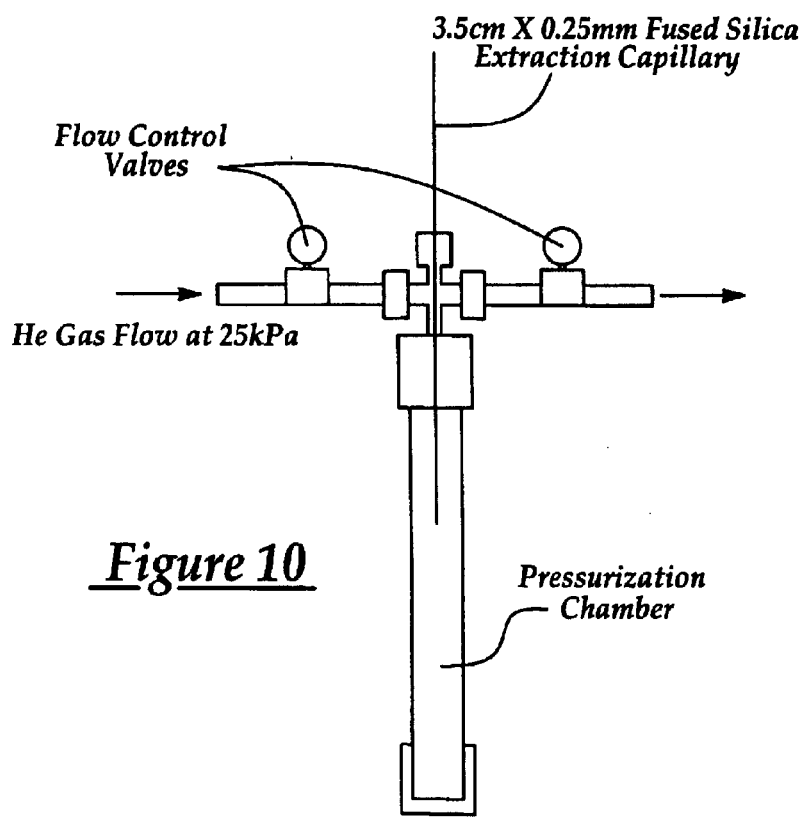
FIG. 10 is a schematic view of a capillary filling/purging device made in accordance with the present invention.

Preparation of Sol-gel Coated Capillaries. Sol-gel PDMS and PEG extraction capillaries, as well as the sol-gel open-tubular GC columns, were prepared according to procedures described elsewhere. (Wang, D.-X.; Chong, S.-L.; Malik, A. *Anal. Chem.* 1997, 69, 4566–4576; Shende, C.; Kabir, A.; Hamlet, C.; Malik, A. *Manuscripi in preparation*) Briefly a previously cleaned and hydrothermally treated fused silica capillary was filled with a specially designed sol solution using a helium pressure operated filling/purging device (FIG. 10). The sol solution was prepared by dissolving appropriate amounts of a sol-gel precursor (e.g., methyltrimethoxysilane), a sol-gel-active organic polymer (e.g., hydroxyterminated polydimethylsiloxane), a surface deactivation reagent (e.g., polymethylhydrosiloxane), and a sol-gel catalyst (e.g., trifluoroacetic acid) in a suitable solvent system. After filling, the sol solution was allowed to stay inside the capillary for 20–30 minutes. During this residence time, an organic-inorganic hybrid sol-gel network evolves in the sol solution within the confined environment of the fused silica capillary, and a this layer of this sol-gel stationary phase evolving in close vicinity of the capillary walls gets chemically bonded to it as a result of condensation reaction with the silanol groups on the capillary inner surface. After this residence period, the residual sol solution was expelled form the capillary under helium pressure using the filling/purging device.

The sol-gel coated capillary was further purged with helium for one hour, and conditioned in a GC over using temperature programming (from 40° C. @ 1° C./min). The capillary was held at the final temperature (350° C. for sol-gel PDMS and 300° C. for sol-gel PEG) for five hours. During conditioning, the capillary was constantly purged with helium at a linear velocity of 20 cm/s. Before using for extraction, the capillary was sequentially rinsed with methylene chloride and methanol followed by drying the capillary in a stream of helium under temperature programming (from 40° C. to 250° C., @ 4° C./min, 60 min at 250° C.).

Gravity-Fed Sample Reservoir for Capillary Microextraction. The gravity-fed sample reservoir for capillary microextraction (FIG. 9) was made by in-house modification of a Chromaflex AQ column (Kontes Glass Co., N.J.) consisting of a thick-walled glass cylinder coaxially placed inside an acrylic jacket. For this, the bottom screw caps, jacket sealing rings, vinyl o-rings, nylon bed support, and acrylic jacket were removed form the Chromaflex AQ column. The thick walled glass column was unscrewed and its inner surface was deactivated using a 5% v/v solution of HMDS in methylene chloride. First, the inner walls of the glass were rinsed with the HMDS solution. This was followed by temperature-programmed heating of the column from 40° C. to 300° C. at 1° C./min with a hold-time of 3 hours at the final temperature. The deactivated glass column was then sequentially rinsed with 10 mL each of methylene chloride and methanol to remove any excess residue. The heavy walled glass column was further heated at 250° C. for 1 hour. The column was then cooled down to ambient temperature, thoroughly rinsed with liberal amounts of deionized water, and dried in a helium flow. The entire Chromaflex AQ column was subsequently reassembled. The PEEK tubing nut was removed from the bottom screw cap of the Chromaflex AQ column. A piece of 2"×0.02"i.d.×0.062" o.d. PEEK tubing was cut, and a polypropylene ferrule was placed on one end of the tubing. The tubing was placed through a connecting plastic nut. The extraction capillary was placed into the tubing leaving a 1 cm portion extending out fro the bottom and a 05. cm portion from the top. The connecting plastic nut was screwed tightly into the bottom screw cap of the Chromaflex AQ column to ensure a leak-free connection.

Thermal Desorption of Extracted Analytes in the GC Injection Port. To facilitate thermal desorption of the extracted analytes from sol-gel microextraction capillary for their subsequent introduction into the GC capillary column, the Varian Model 1079 split/splitless injector was slightly modified. For this, the quartz wool was removed from the glass insert to accommodate a two-way fused silica connector within the insert. With the glass insert (now without the quartz wool) in place, the injection port was cooled down to ambient temperature. The metallic nut at the top of the injector together with the rubber septum, the septum support, and the glass insert were temporarily removed from the injection port. The injector end of the GC capillary column was then pushed for the bottom of the injector to pass it through the injection port and the glass insert (now located outside the port) such that about 10–15 cm of the capillary column and extends out from the top of the insert. This end of the column was press-fitted into the lower end of the deactivated two-way fused silica connector. The two-way connector with press-fitted column end was then secured inside the glass insert, which was subsequently placed back into injection port so that the two-way butt connector with the attached GC column head remained within the glass insert. The septum support was replaced on top of the glass insert. The septum was replaced and the injector nut was tightened down. Finally, the capillary column was secured inside the oven by tightening the ferrule connection at the bottom of the injection port. After performing capillary microextraction, the extraction capillary was connected to the system in the following way. The capillary column nut at the bottom of the injector was loosened and the column was slid up. The extraction capillary was passed through the septum support and pressed-fitted into the fused silica two-way butt connector. The column was then pulled down until the extraction capillary disappeared below the septum support, and remained inside the glass insert (FIG. 10). The septum was replaced, and the injector nut and the capillary column nut were tightened down.

Sol-gel Capillary Microextraction-GC Analysis. Sol-gel PDMS and sol-gel PEG-coated capillaries were used for extraction. Prior to extraction, the sol-gel coated extraction capillary was first thermally conditioned with a simultaneous flow of helium through it. This involved using helium carrier gas at 10 psi and setting the initial GC temperature at 40° C. with the extraction capillary connected to the injection port. The GC temperature was increased at a rate of 5°

C./min until 250° C. was reached. The rate of GC temperature increase was then changed to 1° C./min. For sol-gel PDMS- and sol-gel PEG-coated capillaries the final conditioning temperatures were 350° C., and 300° C., respectively. The extraction capillaries were held at the final temperatures for 60 minutes with continuous helium flow through them.

After conditioning, the extraction capillary was cooled to room temperature, removed from the GC, and installed on the homemade sample reservoir (FIG. 9).

To perform capillary microextraction the extraction capillary was vertically connected to the empty reservoir by removing the PEEK tubing nut from the bottom screw cap, inserting the capillary into the peek tubing (so that ~1 cm of capillary remained extended form the bottom and ~0.5 cm from the top of the tubing), and reassembling the apparatus. The aqueous sample (25 mL) was placed in the reservoir, and allowed to flow through the extraction capillary under gravity for 30 minutes for equilibrium to be established. After this, the microextraction capillary was removed from the gravity-fed apparatus and immediately connected to the homemade capillary filling/purging device (FIG. 2). The extraction capillary was purged with helium gas at 25 kPa for 1 minute to remove any excess sample solution. The outer surface of the extraction capillary was wiped clean just before connecting it to the top end of a two-way press-fit fused silica connector placed in temperature programmable split/splitless injector port of the GC, the column inlet being connected to the bottom end of the two-way fused silica connector.

The extracted analytes were then thermally desorbed from the capillary by rapid temperature programming of the injector (@ 100° C./min starting from 30° C.). The nature of the coating used in the capillary determined final temperature of the ramp (330° C. for sol-gel PDMS- and 280° C. for sol-gel PEG-coated capillaries). The desorption was performed over the five-minute period whereby the released analytes were swept over by the carrier gas into the GC column. The thermal desorption step was accomplished in the splitless mode, keeping the column temperature at 30° C. to promote effective solute focusing at the column inlet. After thermal desorption, the split vent remained closed throughout the course of the chromatographic run. The GC separations were performed using in-house prepared sol-gel-coated open tubular PDMS columns (10 m×0.25 mm i.d.). After the sample was introduced into the column, the column oven temperature was increased at a rate of 15° C./min. GC analysis were carried out using helium as the carrier gas. Analyte detection was performed using a flame ionization detector (FID). The FID detector temperature was maintained at 350° C.

Results and Discussion. Sol-gel technology provides an elegant synthetic pathway to advanced materials (Novak, B. M. Adv. Mater. 1993, 5, 422–433; Livage, J. In Applications of Organometallic Chemistry in the Preparation and Processing of Advanced Materials, Harrod, J. F., Laine, R. M. Eds.; Kluwer: Dordrecht, The Netherlands, 1995; pp.3–25; Walsh, D.; Whiton, N. T. Chem. Mater. 1997, 9, 2300–2310) with a wide range of applications. (Aylott, J. W.; Richardson, D. J.; Russell, D. A. Chem. Mater. 1997, 9, 2261–2263; Collinson, M. M.; Howells, A. R. Anal. Chem. 2000, 72, 702A–709A; Lobnik, A.; Wolfbeis, O. S. Sens. Actuators B 1998, 51, 203–207; Vorotilov, K. A.; Petrovsky, V. I.; Vasiliev, V. A.; Sobolevsky, M. V. J. Sol-gel Sci. Technol. 1997, 8, 581–584; Reisfeld, R.; Jorgenson, C. K. (eds.), Spectroscopy, Chemistry, and Applications of Sol-gel Glasses, Springer-Verlag, Berlin, 1992; Lev, O.; Bharathi, S.; Glezer, V.; Modestove, A.; Gun, J.; Rabinovich, L.; Sampath, S. Chem. Mater. 1997, 9, 2354–2375; Atik, M.; Luna, F. P.; Messaddeq, S. H.; Aegerter, M. A. J. Sol. Gel. Sci. Technol. 1997, 8, 517–522; Haruvy, Y.; Gilath, I.; Maniewictz, M.; Eisenberg, N. Chem. Mater. 1997, 9, 2604–2615; Fabes, B. D.; Uhlmann, D. R. J. Am. Ceram. Soc. 1990, 73, 978–988; Sakka, S.; Yoko, T. In Chemistry, Spectroscopy, and Applications, Reisfeld, R., Jorgenson C. K. Eds.; Springer-Verlag: Berlin, 1992; pp.89–118) In the context of analytical microseparations, it allows for the in situ creation of hybrid organic-inorganic stationary phases within separation columns in the form of coatings, (Rodriguez, S. A.; Colon, L. A. Chem. Mater. 1999, 11, 754–762; Rodriguez, S. A.; Colon, L. A. Anal. Chem. Acta 1999, 397, 207–215; Guo, Y.; Colon, L. A. J. Microcol. Sep. 1995, 7, 485–491; Guo, Y.; Colon, L. A. Anal. Chem. 1995, 67, 2511–2516; Guo, Y.; Colon, L. A. Chromatographia 1996, 43, 477–483; Guo, Y.; Imahori, G. A.; Colon, L. A. J. Chromatogr. A. 1996, 744, 17–29; Narang, P.; Colon, L. A. J. Chromatogr. A. 1997, 773, 65–72; Hayes, J. D.; Malik, A. J. Chromatogr. B 1997, 695, 3–13; Hayes, J. D.; Malik, A. Anal. Chem. 2001, 73, 987–996) monolithic beds, (Cortes, H. J.; Pfeiffer, C. D.; Richter, B. E.; Stevens, T. S. J. High. Resolut. Chromatogr. Chromatogr. Commun. 1987, 10, 446–448; Fields, S. M. Anal. Chem. 1996, 68, 2709–2712; Hayes, J. D.; Malik, A. Anal Chem. 2000, 72, 4090–4099; Nakanishi, K.; Minakuchi, H.; Soga, N.; Tanaka, N. J. Sol. gel. Sci. Technol 1997, 8, 547–552; Dulay, M. T.; Kulkarni, R. P.; Zare, R. N. Anal. Chem. 1998, 70, 5103–5107; Fujimoto, C. J. High Resol. Chromatogr. 2000, 23, 89–92; Roed, L.; Lundanes, E.; Greibrokk, T. J. Micro Sep. 2000, 12, 561–567) and stationary phase particles. (Reynolds, K. J.; Colon, L. A. J. Liq. Chromatogr. & Rel. Technol. 2000, 23, 161–173; Pursch, M.; Jager, A.; Schneller, T.; Brindle, R.; Albert, K.; Lindner, E. Chem. Mater. 1996, 8, 1245–1249) Excellent chromatographic and electromigration separations have been demonstrated using separation columns with sol-gel stationary phases. (Wang, D. X. *Sol-gel Chemistry-Mediated Novel Approach to Column Technology for High-Resolution Capillary Gas Chromatography*, Ph.D. Dissertation, University of South Florida, Department of Chemistry: Tampa, Fla., 2000; Wang, D.-X.; Chong, S.-L.; Malik, A. Anal Chem. 1997, 69, 4566–4576; Guo, Y.; Colon, L. A. Anal. Chem. 1995, 67, 2511–2516; Hayes, J. D.; Malik, A. J. Chromatogr. B 1997, 695, 3–13; Hayes, J. D.; Malik, A. Anal Chem. 2001, 73, 987–996; Hayes, J. D. "*Sol-Gel Chemistry-Mediated Novel Approach to Column Technology for Electromigration Separations*," Ph.D. dissertation, Department of Chemistry, University of South Florida, Tampa, Fla., USA, 2000; Tang, Q.; Xin, B.; Le, M. L. J. Chromatogr. A 1999, 837, 35–50; Cabrera, K.; Lubda, D.; Eggenweiler, H.-M.; Minakuchi, H.; Nakanishi, K. J. High Resol Chromatogr. 2000, 23, 93–99; Chen, Z.; Hobo, T. Anal Chem. 2001, 73, 3348–3357; Roed, L.; Lundanes, E.; Greibrokk, J. Chromatogr. A 2000, 890, 347–353.) Applicants introduced sol-gel coatings for gas chromatography (Wang, D.-X.; Chong, S.-L.; Malik, A. Anal. Chem. 1997, 69, 4566–4576) and solid-phase microextraction (Chong, S. L.; Wang, D.-.X.; Hayes, J. D.; Wilhite, B. W.; Malik, A. Anal. Chem. 1997, 69, 3889–3898) in 1997, and demonstrated significant thermal and solvent stability advantages inherent in sol-gel coated GC columns (Wang, D. X. *Sol-gel Chemistry-Mediated Novel Approach to Column Technology for High-Resolution Capillary Gas Chromatography*, Ph.D. Dissertation, University of South Florida, Department of Chemistry: Tampa, Fla., 2000) and SPME fibers. (Malik, A.; Chong, S.-L. In *Applications of*

*Solid-phase Microextraction*, Pawliszyn, J. Ed.; Royal Society of Chemistry (RSC): Cambridge (UK), 1999; pp.73–91) Since then several other groups have got involved in sol-gel research for solid phase microextraction (Gbatu, T. P.; Sutton, K. L.; Caruso, J. A. *Anal. Chim. Acta* 1999, 402, 67–79; Wang, Z. Y.; Xiao, C. H.; Wu, C. Y.; Wu, C.; Han, H. *J. Chromatogr. A* 2000, 893, 157–168; Zeng, Z.; Qiu, W.; Huang, Z. *Anal. Chem.* 2001, 73, 2429–2436) and solid-phase extraction. (Senevirante, J.; Cox, J. A. Talanta 2000, 52, 801–806) Because of the advanced material properties, sol-gel coatings and monolithic beds can also be expected to serve as excellent extraction media in a capillaries as an effective mans of solventless microextraction, and call such a microextraction technique as Sol-gel Open Tubular Microextraction (OTME). Sol-gel OTME is synonymous with in-tube solid-phase microextraction (in-tube SPME) on sol-gel coated capillaries. Both sol-gel OTME and sol-gel monolithic microextration (MME) can be combined under a general term—Capillary Microextraction (CME). The new terminology provides a better reflection of the techniques, since "In-Tube Solid-phase Microextraction" is not necessary limited to the use of only "solid phases" as the extraction media. In fact, liquid stationary phase coatings are commonly used both in in-tube SPME as well as conventional SPME.

Sol-gel technology allows of the creation of coatings on the inner surface of open tubular GC, CE, and CEC columns (Wang, D.-X.; Chong, S.-L.; Malik, A. *Anal. Chem.* 1997, 69, 4566–4576; Guo, Y.; Colon, L. A. *Anal. Chem.* 1995, 67, 2511–2516; Hayes, J. D.; Malik, A. *Anal. Chem.* 2001, 73, 987–996) as well as on the outer surface of substrates of different shapes and geometry (e.g., SPME fibers. (Chong, S. L.; Wang, D.-.X.; Hayes, J. D.; Wilhite, B. W.; Malik, A. *Anal. Chem.* 1997, 69, 3889–3898; Gbatu, T. P.; Sutton, K. L.; Caruso, J. A. *Anal. Chim. Acta* 1999, 402, 67–79; Wang, Z. Y.; Xiao, C. H.; Wu, C. Y.; Wu, C.; Han, H. *J. Chromatogr. A* 2000, 893, 157–168; Zeng, Z.; Qiu, W.; Huang, Z. *Anal. Chem.* 2001, 73, 2429–2436.). It is applicable to the creation of silica-based, (Iler, R. K. *The Chemistry of Silica*, Wiley, N.Y., 1979; Brinker, C. J.; Scherer, G. W. *Sol-Gel Science*, Academic Press, San Diego, Calif., 1990; Rabinovich, E. M. In *Sol Gel Technology for Thin Films, fibers, Preforms, Electronics, and Specialty Shapes*, Klein, L. C. Ed.; Noyes Publications: Park Ridge, N.J., 1988; pp. 260–294) and transition metal-based (Livage, J.; Henry, M.; Sanchez, C. *Prog. Solid. St. Chem.* 1988, 18, 259–341; In, M.; Gerardin, C.; Lambard, J.; Sanchez, C. *J. Sol. gel. Sci. Technol* 1995, 5, 101–114; Jiang, Z.-.; Zuo, Y.-. *Anal. Chem.* 2001, 73, 686–688; Silva, R. B.; Gushikem, Y.; Collins, C. H. *J. Sep. Sci.* 2001, 24, 49–54; Palkar, V. R. *Nanostructured Mater.* 1999, 11, 369–374; Chaput, F.; Dunn, B.; Fuqua, P.; Salloux, K. *J. Non. Cryst. Solids.* 1995, 188, 11–18) and silica/nonsilica mixed systems. (Dutoit, D.C.; Schneider, M.; Baiker, A. *J. Catal.* 1995, 153, 165–176; Jones, S. A.; Wong, S.; Burlitch, J. M.; Viswanathan, S.; Kohlstedt, D. L. *Chem. Mater.* 1997, 9, 2567–2576; Kosuge, K.; Singh, P. S. *J. Phys. Chem. B* 1 999, 103, 3562–3569) In the context of capillary separation and sample preconcentration techniques, the most important attribute of sol-gel coating technology is that it provides surface coatings that become automatically bonded to the substrate surfaces containing sol-gel-active functional groups (e.g., silonal groups). This direct chemical bonding results in enhanced thermal and solvent stability of sol-gel coatings. The attributes of thermal and solvent stability of the stationary phase coatings are enormously important in analytical separation and sample preconcentration.

Sol-gel technology also allows for the stationary phase coating, its immobilization, and deactivation to be achieved in one single step (Wang, D.-X.; Chong, S.-L.; Malik, A. *Anal. Chem.* 1997, 69, 4566–4576) instead of multiple time-consuming steps involved in conventional coating technology.

The use of the stationary phase coating on the inner surface of a fused silica capillary eliminates coating scraping problem inherent in fiber-based SPME and significantly reduces the possibility of sample contamination. Furthermore, the protective polyimide coating on the outer surface of the fused silica extraction capillary adds flexibility to the extraction device as compared with traditional SPME fibers.

Sol-gel PDMS- and PEG-coated were used in conjunction with the gravity-fed sample reservoir (FIG. 9) to develop a simple and reproducible method for the extraction of analytes form aqueous media. The aim was to make a contribution to the further development of SPME technology by using sol-gel extraction media whose advanced material properties would help to overcome some basic problems inherent either in fiber-based SPME or in-tube with conventional coatings. Current status of SPME technology clearly calls for the improvement of sample capacity of the fiber, enhancement of thermal and solvent stability of the coating, and providing better protection against mechanical damage of the coating. The present data demonstrates the possibility of addressing these shortcomings of conventional SPME via sol-gel capillary microextraction (CME).

Sol-gel capillary microextraction typically uses a short length of fused silica capillary coated internally with sol-gel stationary phase. The extraction is carried out by attaching the extraction capillary to an in-house designed gravity-fed extraction apparatus (FIG. 9). Sol-gel-coated capillary coatings are chemically bonded to the substrate, stabilizing the coating during operations that require exposure to high temperatures or organic solvents. Because of the chemical bonding, sol-gel coatings have significant stability advantage over physically held or glued coatings (Liu, Y.; Shen, Y.; Lee, M. L. *Anal. Chem.* 1997, 69, 190–195) used in SPME practice. Upelco recommends that commercial PDMS fibers should be not be exposed to non-polar organic solvents like hexane. (SUPELCO Catalog 2001: *Chromatography Products for Analysis and Purification*, Aldrich-Sigma Co.: USA, 2001; p.259)

Figure 11A:
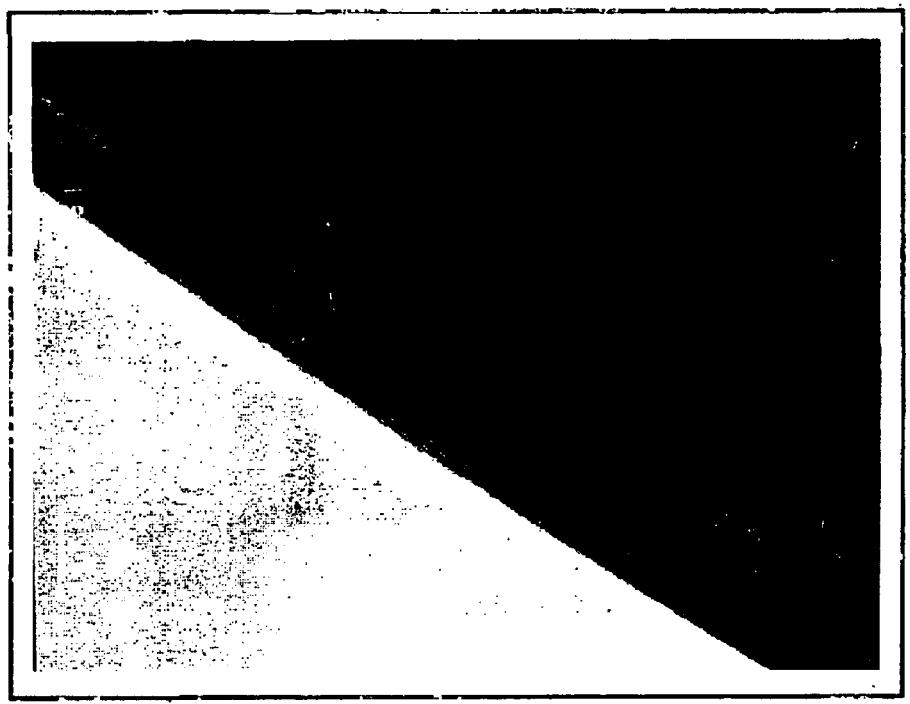
FIG. 11 is a scanning electron microscopic image of 250 $\mu$m i.d. microextraction capillaries with sol-gel PDMS in FIG. 11A and sol-gel PEG, as shown in FIG. 11B coatings, magnification being 10,000×.
Figure 11B:
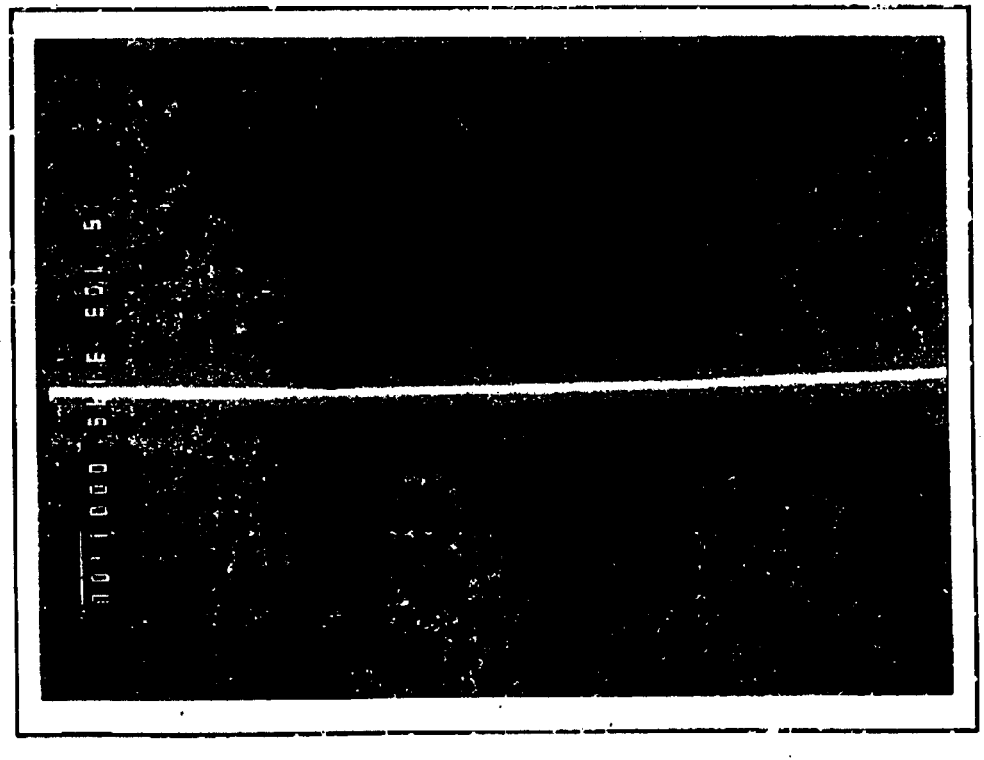

FIG. 11 represents scanning electron micrographs (SEM) illustrating the internal structures two 250 $\mu$m i.d. fused silica capillaries with sol-gel PDMS (FIG. 11A) and sol-gel PEG (FIG. 11B) coatings on the inner surface. As can be seen from these SEM images, the coatings in these microextraction capillaries are remarkably uniform in thickness. The thickness of the sol-gel PDMS coating was estimated approximately at 0.6 $\mu$m, while that for the sol-gel PEG coating-at~0.4 $\mu$m.

Figure 12:
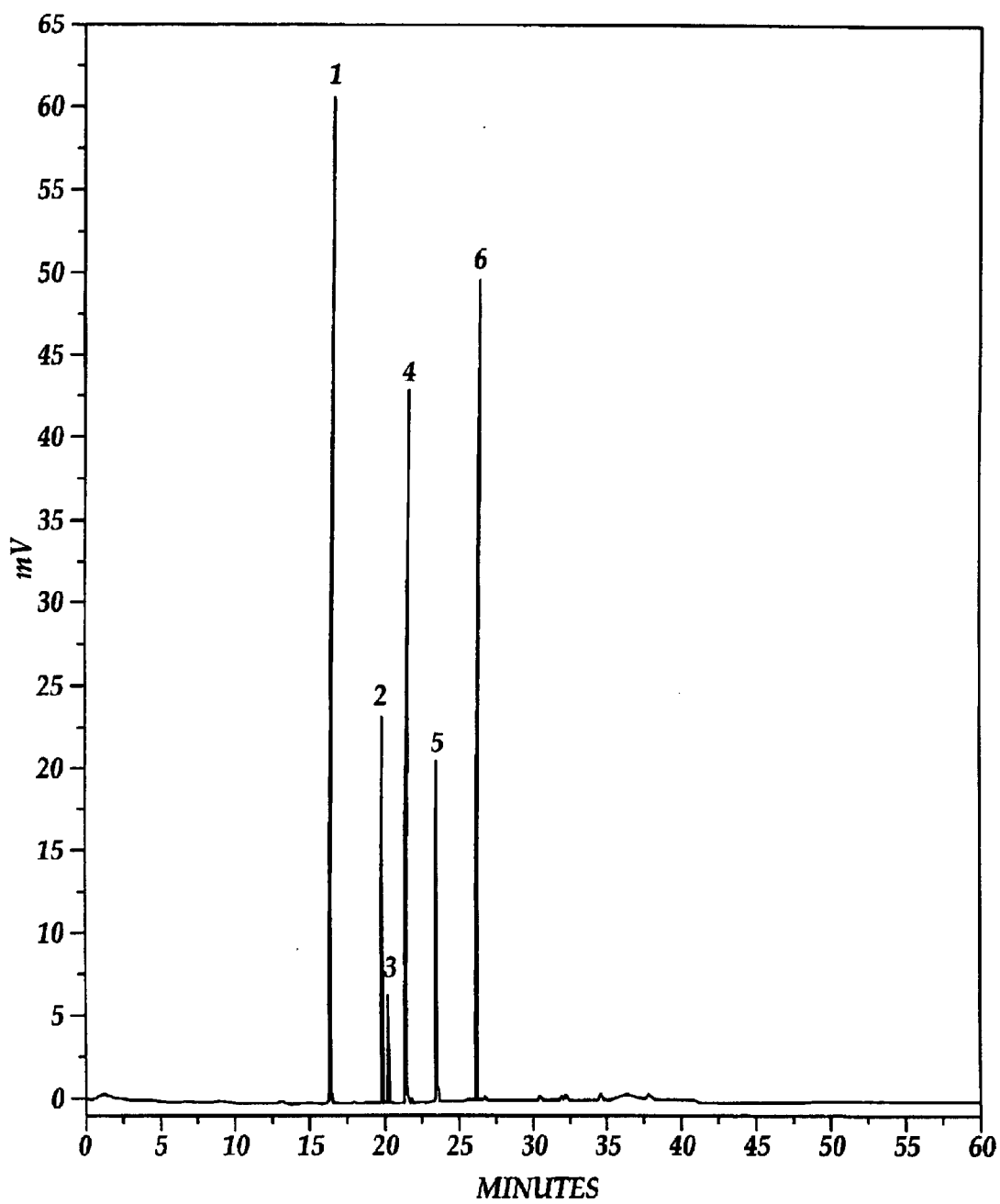
FIG. 12 is a capillary microextraction analysis of PAH's at ppb- and sub-ppb level concentrations using a sol-gel PDMS coated capillary made in accordance with the present invention.

FIG. 12 and Table I present experimental data that illustrates open tubular microextraction of polycyclic aromatic hydrocarbons (PAHs) performed on an aqueous sample at ppb and sub-ppb level concentrations of the analytes using a sol-gel PDMS coated capillary. The repeatability data present in Table I shows that sol-gel OTME-GC provides excellent run-to-run repeatability in solute peak areas (less than 3%) and retention time (less than 0.2%). The data on the detection limits demonstrate high sensitivity of capillary microextraction. For example, using a flame ionization detector, the detection limit for naphthaline (peak #1 in FIG. 12) was estimated at 300 parts per quadrillion (ppq). This ppq level sensitivity of CME was obtained on a 250 $\mu$m i.d. capillary with relatively thin coating (0.6 $\mu$m).

Sol-gel coating technology can easily produce thick coatings (Chong, S. L.; Wang, D.-.X.; Hayes, J. D.; Wilhite, B.

W.; Malik, A. *Anal Chem.* 1997, 69, 3889–3898; Wang, Z. Y.; Xiao, C. H.; Wu, C. Y.; Wu, C.; Han, H. *J. Chromatogr. A* 2000, 893, 157–168; Zeng, Z.; Qiu, W.; Huang, Z. *Anal. Chem.* 2001, 73, 2429–2436) ($d_f$>1 µm). For example, Zeng et al. recently reported SPME on sol-gel coated fibers with a coating thickness of 76 µm. The use of microextraction capillaries with thick sol-gel coatings should lead to higher sensitivity of capillary microextraction as will be demonstrated in an upcoming paper. (Medlar, J.; Kabir, A.; Malik, A. *Work in Progress*) It can be expected that the use of capillaries with larger inner diameter and thicker sol-gel coatings should lead to further enhancement of this extraction sensitivity.

In this work, the extraction capillary length was relatively short—only 3.5 cm. The use of such a short length was dictated by the linear dimensions of the glass insert of the injection port and that of the press-fit connector. In principle longer extraction capillaries can be employed using a different configuration of the coupling between the extraction capillary and the open tubular GC column.

Figure 13:
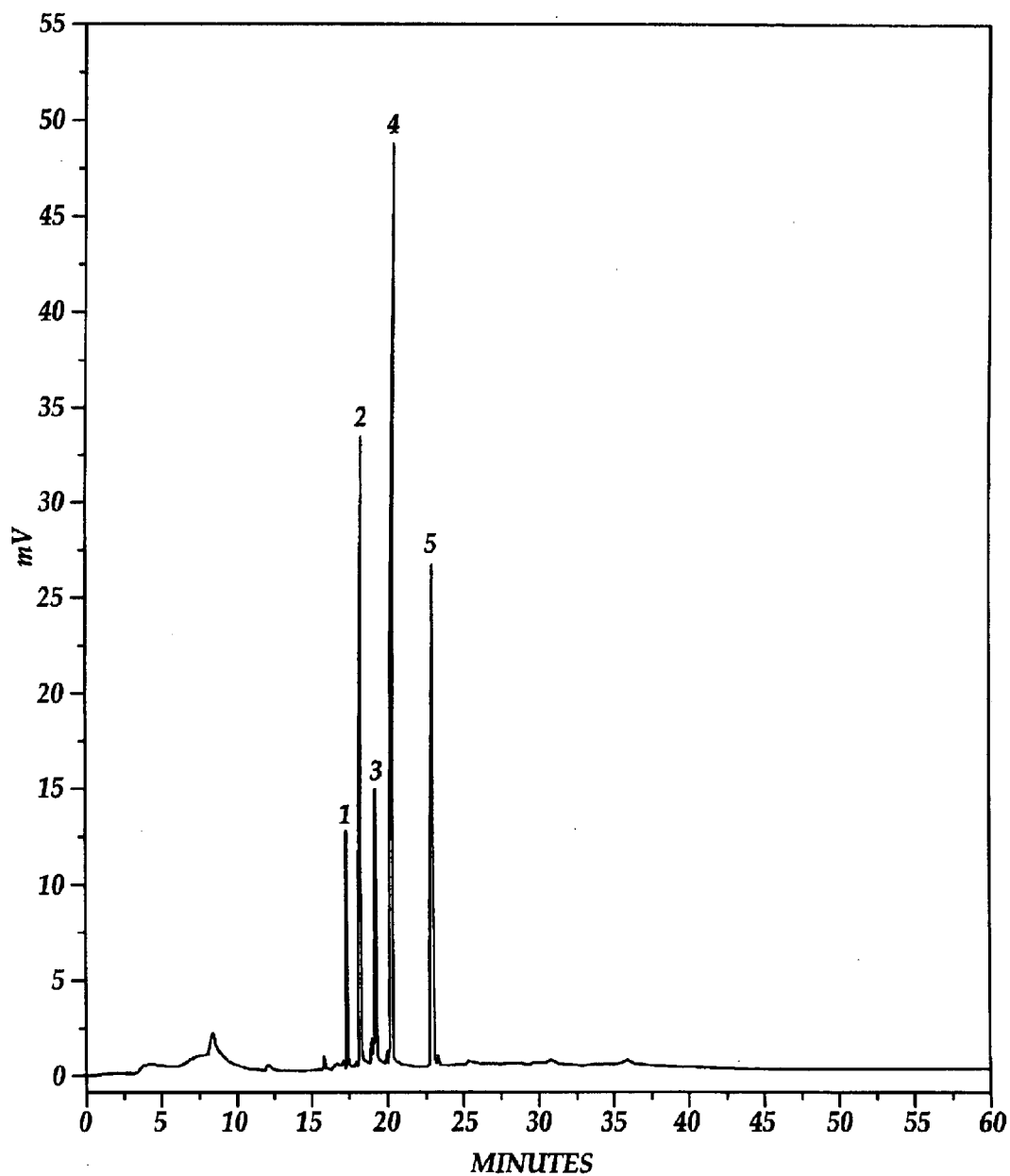
FIG. 13 is a capillary microextraction analysis of aldehydes using a sol-gel PDMS coated capillary at 100 ppb analyte concentration.

FIG. 13 represents a gas chromatogram of several free aldehydes extracted from an aqueous medium by OTME using a sol-gel PDMS coated capillary. Aldehydes are important both form the industrial, environmental, and toxicological points of view. (Koivusalmi, E.; Haatainen, E.; Root, A. *Anal. Chem.* 1999, 71, 86–91; Martos, P. A.; Pawliszyn, J. *Anal. Chem.* 1998, 70, 2311–2320) Low molecular weight aldehydes are starting material for important plastic materials. Formaldehyde represents a ubiquitous indoor air pollutant. (Koziel, J. A.; Noah, J.; Pawliszyn, J. *Environ. Sci. Technol.* 2001, 35, 1481–1486) Aldehydes are major disinfections by-products formed as a result of ozonation of organic contaminants in drinking water (Nawrocki, J. *J. Chromatogr. A* 1996, 749, 157–163; Fielding, M.; Farrimond, M. *Disinfection By-Products in Drinking Water. Current Issues*, Royal Society of Chemistry, Cambridge, UK, 1999) and accurate analysis of their trace-level contents is important due to their carcinogenic activities and other adverse health effects. (*Guidelines for Drinking Water Quality*, 2nd ed. WHO (World Health Organization): Geneva, 1993) Aldehydes are polar compounds, and their determination is often performed through derivatization into less polar and/or easy to detect forms. (Nawrocki, J. *J. Chromatogr. A* 1996, 749, 157–163; Ferioli, F.; Vezzalini, F.; Rustichelli, C.; Gamberini, G. *Chromatographia* 1995, 41, 61–65; Oesterheldt, G.; Pozeg, M.; Bubendorf, A.; Bartoldus, D. *Fres. Z. Anal Chem.* 1985, 321, 553–555) In various sampling and sample preparation techniques (including SPME), the derivatization step is often performed in situ—right on the active matrix of the sampling device. (Zhang, J.; Zhang, L.; Ilacqua, V. *Environ. Sci. Technol.* 2000, 34, 2601–2607) In SPME, this step is carried out on the fiber coating loaded with the derivatizing reagent. Derivatization often results in better affinity of the derivatized forms of the polar analytes (compared with their underivatized forms) for the organic phase on the fiber, and reduces solute adsorption on the chromatographic column used for their subsequent analysis.

In this work, aldehydes were extracted and analyzed without derivatization. This became possible due to outstanding material properties of sol-gel PDMS coating used both in the microextraction capillary as well as in the GC separation column. Organic-inorganic nature of the sol-gel PDMS coating provides sorption sites both of the polar and non-polar analytes. High quality of column deactivation achieved through sol-gel column technology (Wang, D.-X.; Chong, S.-L.; Malik, A. *Anal. Chem.* 1997, 69, 4566–4576) allows the GC analysis of aldehydes without derivatization. From an analytical standpoint, the possibility of extraction and gas chromatographic analysis of underivatized aldehydes by OEME-GC is important, and should provide simplicity, speed, sensitivity, and accuracy in aldehyde analysis.

Figure 14:
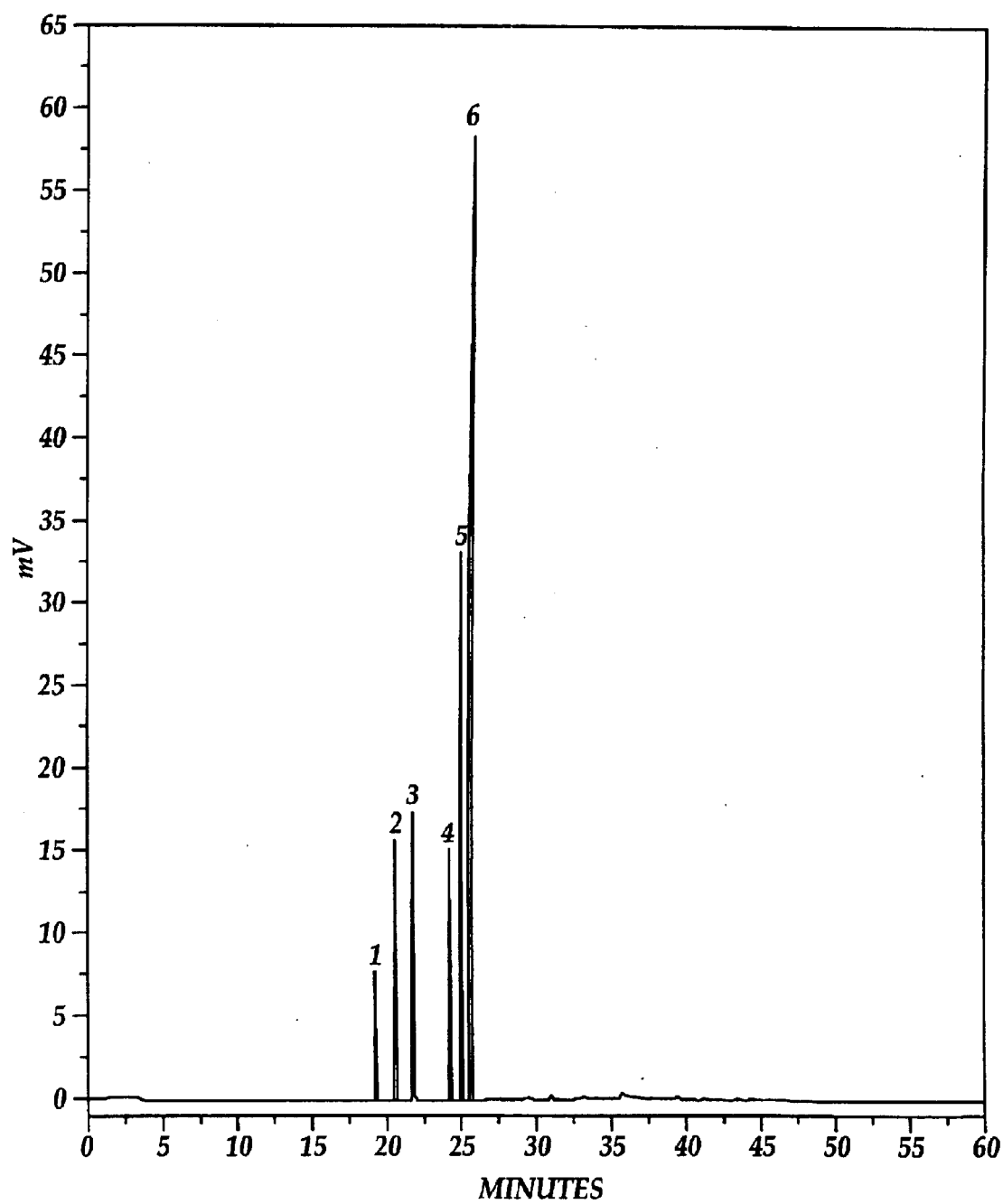
FIG. 14 is a capillary microextraction analysis of ketones using a sol-gel PDMS coated capillary at 100 ppb analyte concentration.

FIG. 14 represents a gas chromatogram illustrating OTME-GC analysis of several ketones extracted form an aqueous sample using a sol-gel coated PDMS capillary. Like aldehydes, ketones are also often derivatized for analysis, (Zhang, J.; Zhang, L.; Ilacqua, V. *Environ. Sci. Technol.* 2000, 34, 2601–2607; Buldt, A.; Kurst, U. *Anal. Chem.* 1999, 71, 1893–1898) especially by HPLC. Using sol-gel coated extraction capillary and separation column, no derivatization step was necessary either at the extraction or the separation step. Two important features can be observed in this chromatogram. First, the peaks are sharp and symmetrical which is indicative of effective focusing of the analytes at column inlet after their desorption as well as excellent performance of the sol-gel PDMS column used for the separation. Second, although all analyte concentrations in the aqueous sample were practically the same (100 ppb), the analyte peak height increased with the increase of the molecular weight of the ketone. This might be the consequence of two distinctive phenomena: (1) higher loss of the more volatile ketones during the post-extraction purging step of the microextraction capillary, and (2) displacement of the lower molecular weight ketones by the ones with higher molecular weights. (Pawliszyn, J. *J. Chromatogr. Sci.* 2000, 37, 270–270.) However, considering the fact that the analyte concentrations were sufficiently low (100 ppb), and that sol-gel coatings are characterized by enhanced surface area, (Chong, S. L.; Wang, D.-.X.; Hayes, J. D.; Wilhite, B. W.; Malik, A. *Anal. Chem.* 1997, 69, 3889–3898) it is not likely that the coating was overloaded at this concentration level. So, it is more likely that the peak size discrimination of the ketones was caused primarily by the first factor.

The sol-gel OTME-GC for aldehydes and ketones described herein provides a number of important advantages over sample preparation techniques coupled to HPLC. First, the fact that no derivatization is needed makes the procedure faster, simpler, and more accurate. Second, since the flame ionization detector used for GC analysis inherently possess several order of magnitude higher sensitivity compared with the UV detector commonly used with the HPLC analysis, the described procedure also provides sensitivity advantage. The OTME-GC analysis of the aldehydes and ketones is also characterized by low run-to-run RSD values (Table II). For five replicate measurements, RSD values of under 6% and 0.4% were obtained for solute peak area and retention time, respectively, the only exception was benzaldehyde that had a retention time RSD value of 1.9% which is significantly higher than the RSD values for the rest of the aldehydes and ketones studied. At this time, we do not have a good explanation for this anomalous behavior of benzaldehyde.

Figure 15:
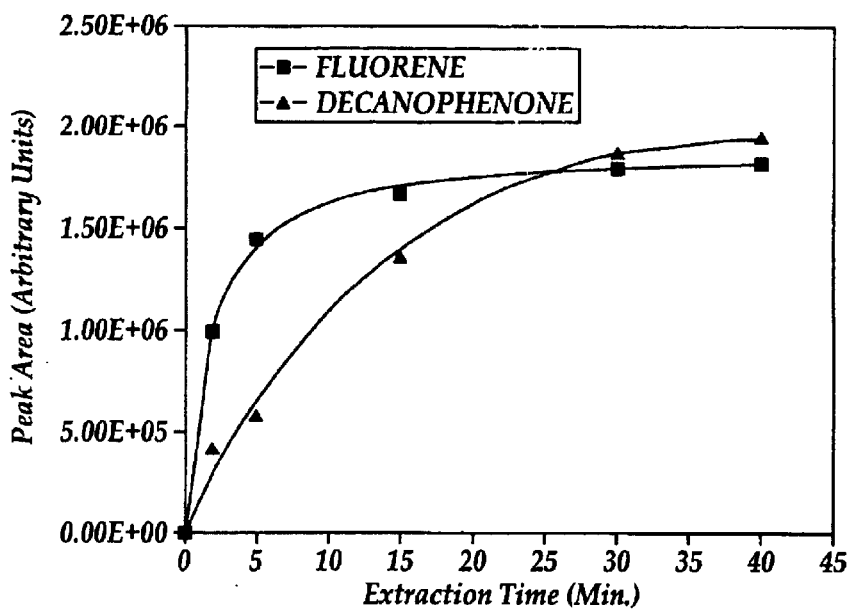
FIG. 15 is an illustration of extraction kinetics of fluorene and decanophenone (▲) obtained on a 3.5 cm×250 $\mu$m i.d. sol-gel PDMS coated microextraction capillary using 1 ppm aqueous solutions.

FIG. 15 illustrates the extraction kinetics of flourene (a non-polar analyte) and decanophenone (a moderately polar analyte) on a sol-gel PDMS coated microextraction capillary. The extraction was carried out using an aqueous sample containing 1 ppm concentration of each analyte. As can be seen from FIG. 15, the extraction equilibrium for Fluorene was practically reached after 15 minutes of extraction while for decanophenone it required about 35 minutes of extraction to reach the plateau on the extraction curve. Such differences in the extraction behavior of the two analytes can be explained based on the differences in their hydrophobilicity. Highly non-polar nature of flourene makes it more susceptible to hydrophobic interaction, and facilitates its extraction by the non-polar PDMS moieties on the sol-gel coating. This is evident from the steeply rising beginning part of the flourene extraction curve in FIG. 15. Higher polarity of the ketone makes it more hydrophilic which leads to a slower extraction process as is evidenced by the more gradually rising nature of the extraction curve of the ketone.

Highly polar compounds, such as alcohols, amines, and phenols, have higher affinity for water. Conventional non-polar phases (e.g., PDMS) are usually not very efficient for their extraction from an aqueous phase. Polar coatings are normally used for the extraction of these highly polar analytes. However, creation of thick coatings of polar stationary phases and their immobilization on a substrate are associated with technical difficulties. (Janak, K.; Horka, M.; Krejci, M. *J. Microcol. Sep.* 1991, 3, 115–120) Previously, Applicants showed (Chong, S. L.; Wang, D.-.X.; Hayes, J. D.; Wilhite, B. W.; Malik, A. *Anal. Chem.* 1997, 69, 3889–3898; Janak, et al, 1991) that these polar compounds can be satisfactorily extracted and analyzed using sol-gel PDMS coatings. This becomes possible thanks to the organic-inorganic hybrid nature of the sol-gel PDMS coatings characterized by the presence of both polar and non-polar sorption sites. Sol-gel coating technology allows for the creation of both polar (Hayes, J. D.; Malik, A. *J. Chromatogr. B* 1997, 695, 3–13; Wang, Z. Y.; Xiao, C. H.; Wu, C. Y.; Wu, C.; Han, H. *J. Chromatogr. A* 2000, 893, 157–168) and non-polar (Chong, et al, 1997; Gou, et al, 2000; Wang, D. X., 2000; Wang, D. X. et al., 1997; Hayes, J. D., et al, 2001; Malik, et al, 1999; Gbatu, T. P., et al, 1999) coatings with equal ease and versatility. In the present work, we demonstrate the possibility of efficient extraction of these polar analytes from an aqueous environment using open tubular capillary microextraction on sol-gel polyethylene glycol (sol-gel PEG) coatings.

Figure 16:
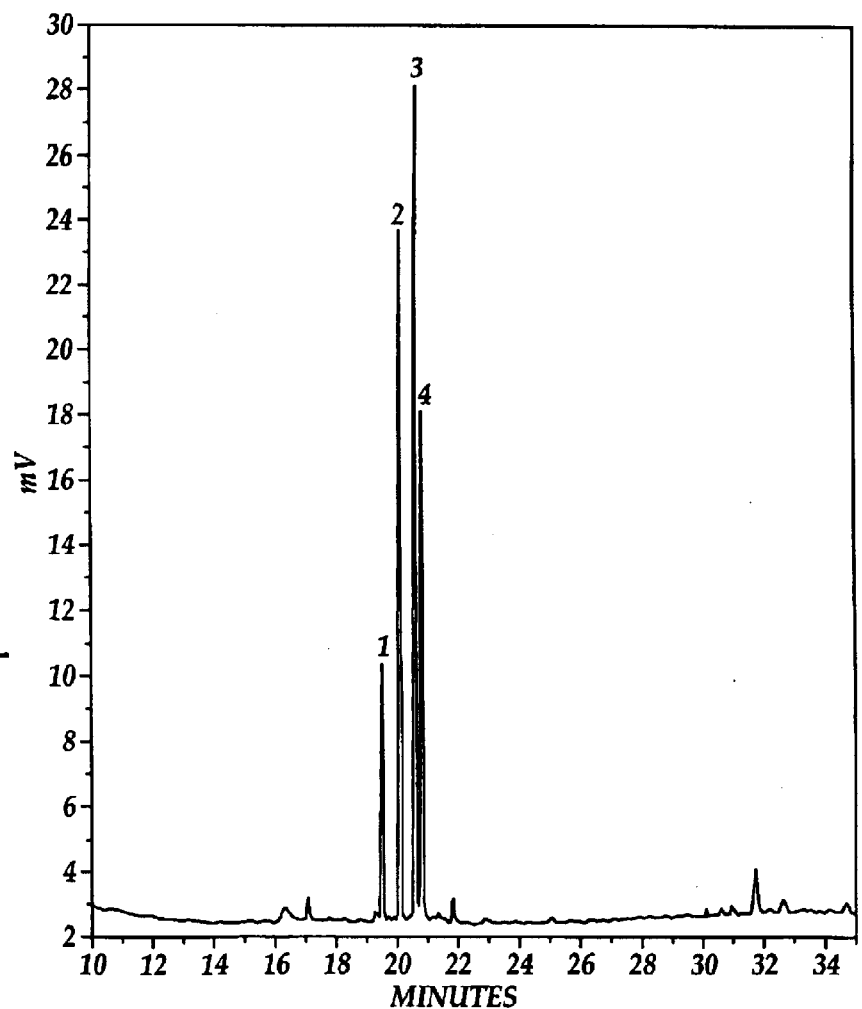
FIG. 16 is a capillary microextraction-GC analysis of dimethylphenol isomers using a sol-gel PEG coated capillary at 10 ppb analyte concentration.

FIG. 16 represents OTME-GC analysis of phenolic compounds at low ppb level concentrations using a sol-gel PEG coated microextraction capillary. A sol-gel PEG coated capillary column was used for their GC analysis. The analysis of phenols is important from an environmental point of view since some phenols are registered in US EPA's priority pollutant list. (EPA Method 604. *Phenols in Federal Register*, Environmental Protection Agency: Friday, Oct. 6, 1984; pp. 58–66) The extraction and GC analysis was done without derivatization, although analysis of polar compounds often require derivatization. (Li, D.; Park, J.; Oh, J.-R. *Anal. Chem.* 2001, 73, 3089–3095; Zapf, A.; Stan, H. J. *J. High Resol. Chromatogr.* 1999, 22, 83–88; Koster, E. H.; Bruins, C. H.; Wemes, C.; de Jong, G. J. *J. Sep. Sci.* 2001, 24, 116–122) Under the used experimental conditions, the detection limit for this analysis was ~10 ppt. The sharp symmetrical peaks and the low detection limits obtained are indicative of high extraction efficiency of the sol-gel PEG coated microextraction capillary and excellent analytical performance of the used sol-gel PEG column. Conventional coatings for the analysis of phenols often show carryover problems (Buchholz, K. D.; Pawlyszyn, J. *Anal. Chem.* 1994, 66, 160–167) because of the strong interaction of polar analytes with the coatings. Effective release of the extracted polar analytes for the coatings require application of high desorption temperature. However, relatively low thermal stability of conventionally prepared thick coatings do not allow of the application of high temperatures during the analyte desorption steps of the analysis, resulting in only partial release to the extracted analytes. This incomplete desorption of the extracted analytes give rise to the carryover problem. The sol-gel PEG-coated extraction capillary showed consistent performance at a desorption temperature of 300° C. No carryover problems were observed fro polar or non-polar analytes on sol-gel PEG as well as sol-gel PDMS coated microextraction capillaries.

Figure 17:
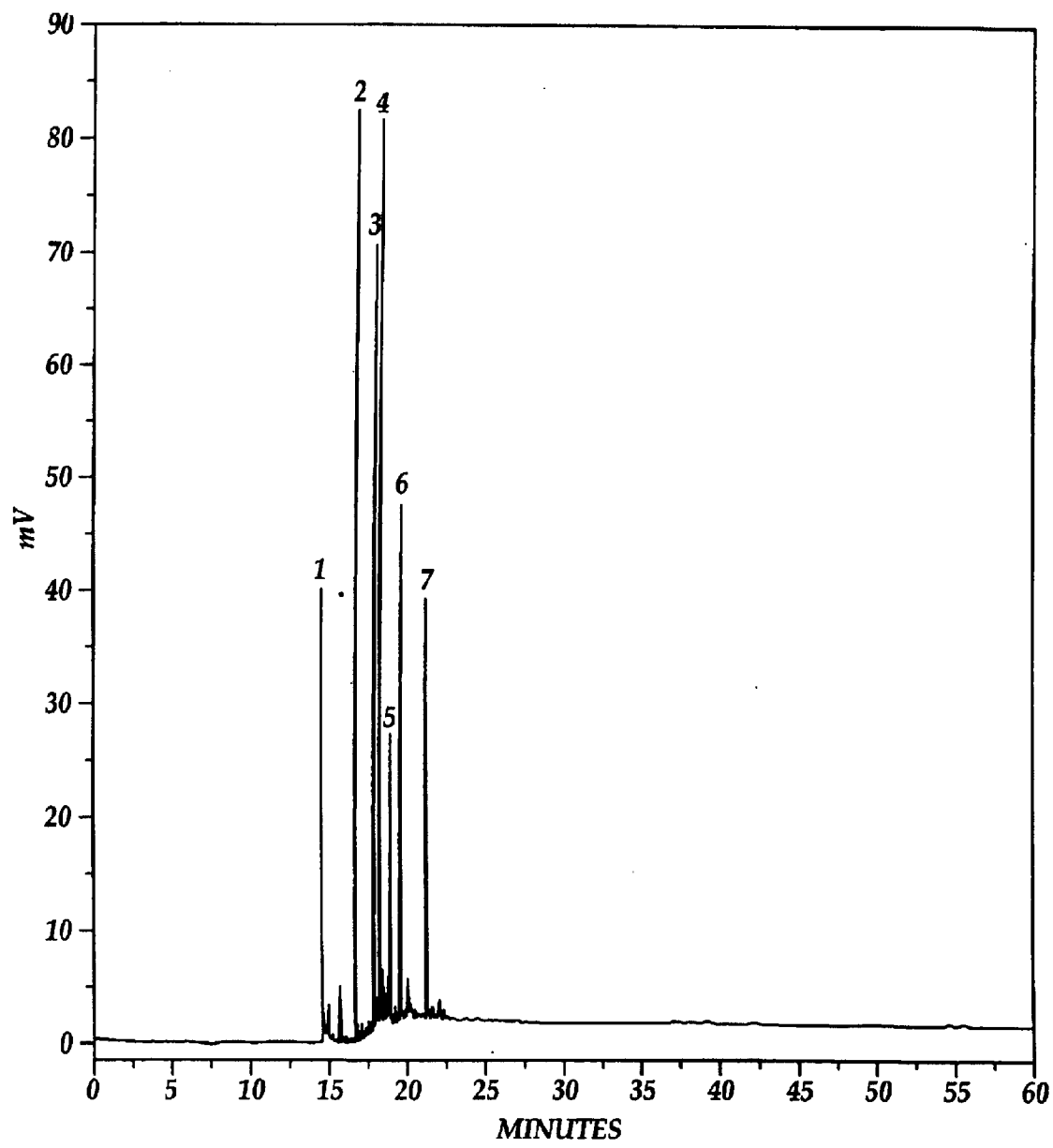
FIG. 17 is a capillary microextraction analysis of alcohol's and amines using a sol-gel PEG coated capillary at 10 ppb analyte concentration.

FIG. 17 illustrates a gas chromatogram of a mixture of alcohols and amines that were extracted from an aqueous medium using a sol-gel PEG coated microextraction capillary. The analytes were at 10 ppb concentration level in the aqueous sample. No derivatization was needed either for extraction or for GC analysis of these highly polar compounds. Excellent peak shapes, detection sensitivity, and extraction efficiency is evident from the chromatographic data presented in FIG. 12 and Table II. The run-to-run repeatability data for the phenols, alcohols and amines, presented in Table II in terms of peak area and retention time RSD values, are also remarkable. For these highly polar analytes, the peak area and retention time RSD values were less than 4.5% and 0.2%, respectively.

The capillary-to-capillary reproducibility for open tubular microextraction was evaluated for the two types of sol-gel coatings used in this work—sol-gel PDMS and sol-gel PDMS and sol-gel PEG coatings. For this, three identical segments of each type of sol-gel coated capillary were used for extraction. Fluorene was used at the test solute for the sol-gel PDMS coated capillary while decanophenone served the same purpose for the sol-gel PEG coated microextraction capillary. A total of six extractions (30 min each) were carried out on each capillary using 1 ppm aqueous solutions containing the respective test solute. The relative standard deviations (RSD) of the mean GC peak area for the two test solute on sol-gel PDMS and sol-gel PEG capillaries were 3.9% and 3.0%, respectively. These low RSD values are indicative of excellent capillary-to-capillary reproducibility in sol-gel open tubular microextraction.

In the present work, OTME was performed using 3.5 cm long sol-gel coated capillary segments. The length of the used extraction capillary was limited by the linear dimensions of the glass insert in the injection port of the used GC (Varian 38000) and the length of the two-way press-fit connector. In this format, the entire length of the extraction capillary was contained inside the GC injection port. However, sol-gel coated capillary segments of greater lengths can be used in GC systems that employ longer glass inserts, (E.g., Shimadzu 17) which should lead to enhanced sensitivity. Even in the present configuration, the coated segment was more than three times longer than coated segments used on conventional SMPE fibers. In an upcoming paper, (Koivusalmi, E.; Haatainen, E.; Root, A. *Anal. Chem.* 1999, 71, 86–91) we will show how desorption of the extracted analytes can be achieved by making a press-fit connection between the extraction capillary and the GC column outside the injection port. Such a configuration will also allow for the use of sol-gel coated capillaries of greater lengths, significantly enhancing the sensitivity of the technique.

For the first time, sol-gel coated capillaries were used for solventless microextraction and sample preconcentration, and the technique was termed sol-gel capillary microextraction (sol-gel CME). Two types of sol-gel coatings (sol-gel PDMS and sol-gel PEG) were effectively used for the extraction of analytes belonging to various chemical classes. Parts per trillion (ppt) and parts per quadrillion (ppq) level detection sensitivities were achieved for polar and non-polar analytes. Further sensitivity enhancements should be possible through the use of thicker sol-gel coatings in conjunction with longer extraction capillaries of larger inner diameter. The sol-gel coated capillaries are characterized by enhanced thermal and solvent stabilities (a prerequisite for efficient analyte desorption), making them very suitable for coupling with both GC and HPLC. Sol-gel capillary microextraction showed remarkable run-to-run and capillary-to-capillary repeatability, and produced peak area RSD values of less than 6% and 4% respectively.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

TABLE I

Peak area and retention time repeatability data for ppb and sub-ppb level concentrations of PAHs, aldehydes, and ketones obtained in five replicate measurements by Capillary Microextraction-GC using sol-gel PDMS coatings.*

| Chemical Class of the Analyte | Name of the analyte | Peak area repeatability (n = 5) | | $t_R$ repeatability (n = 5) | | Detection Limits** |
|---|---|---|---|---|---|---|
| | | Mean peak area (arbitrary unit) | RSD (%) | Mean $t_R$ (min) | RSD (%) | S/N = 3 (ppt) |
| PAHs | Naphthalene | 253244.2 | 2.7 | 16.176 | 0.221 | 0.31 |
| | Acenaphthalene 80% | 73188.9 | 2.5 | 19.170 | 0.169 | 0.66 |
| | Acenaphthene 20% | 19563.4 | 2.9 | 20.112 | 0.181 | 0.58 |
| | Fluorene | 132925.8 | 3.3 | 21.271 | 0.205 | 0.44 |
| | Phenanthrene | 58212.3 | 3.6 | 23.376 | 0.148 | 0.94 |
| | Fluoranthene | 128409.4 | 4.0 | 26.029 | 0.167 | 0.39 |
| Aldehydes | Benzaldehyde | 31013.5 | 6.0 | 16.757 | 1.901 | 103.20 |
| | Nonylaldehyde | 174309.0 | 4.9 | 17.770 | 0.304 | 40.45 |
| | o-tolualdehyde | 64092.1 | 5.3 | 18.860 | 0.309 | 92.35 |
| | n-decylaldehyde | 258555.7 | 4.7 | 19.830 | 0.256 | 28.36 |
| | n-Undecylic aldehyde | 229624.5 | 5.7 | 22.492 | 0.337 | 50.49 |
| Ketones | Valerophenone | 31364.9 | 4.8 | 19.146 | 0.094 | 215.70 |
| | Hexanophenone | 65197.5 | 4.3 | 20.424 | 0.077 | 109.10 |
| | Heptanophenone | 71735.6 | 4.5 | 21.653 | 0.066 | 102.60 |
| | 4'-phenylacetophenone | 43686.8 | 5.6 | 24.189 | 0.035 | 117.20 |
| | Decanophenone | 166995.0 | 4.2 | 24.851 | 0.176 | 55.99 |
| | Anthraquinone | 151529.9 | 3.6 | 25.539 | 0.133 | 32.67 |

*Experimental conditions for capillary microextraction and GC analysis are same as in FIGS. 12 (PAHs), 13 (Aldehydes), and 14 (Ketones).
**Detection limits were calculated for a signal-to-noise ratio (S/N) of 3 using the data presented in FIGS. 12 (PAHs), 13 (Aldehydes), and 14 (Ketones).

TABLE II

Peak area and retention time repeatability data for ppb level concentrations of phenols, alcohols, and amines obtained in five replicate measurements by Capillary Microextraction-GC using sol-gel PEG coatings.*

| Chemical Class of the Analyte | Name of the analyte | Peak area repeatability (n = 5) | | $t_R$ repeatability (n = 5) | | Detection Limits** |
|---|---|---|---|---|---|---|
| | | Mean peak area (arbitrary unit) | RSD (%) | Mean $t_R$ (min) | RSD (%) | S/N = 3 (ppt) |
| Phenols | 2,6-dimethylphenol | 39390.7 | 1.6 | 19.445 | 0.071 | 16.06 |
| | 2,5-dimethylphenol | 86727.4 | 1.5 | 20.016 | 0.097 | 7.085 |
| | 2,3-dimethylphenol | 110890.4 | 1.9 | 20.505 | 0.110 | 6.001 |
| | 3,4-dimethylphenol | 70055.3 | 2.0 | 20.717 | 0.115 | 9.421 |
| Alcohols and Amines | Dicyclohexylamine | 137786.0 | 3.9 | 14.402 | 0.171 | 4.088 |
| | Myristyl ($C_{14}$) alcohol | 135076.9 | 4.2 | 16.524 | 0.152 | 1.992 |
| | Acridine | 138103.6 | 3.8 | 17.728 | 0.153 | 2.318 |
| | Cetyl ($C_{16}$) alcohol | 152309.7 | 4.1 | 18.074 | 0.142 | 2.009 |
| | Benzanilide | 46488.7 | 4.0 | 18.768 | 0.161 | 5.976 |
| | Stearyl ($C_{18}$) alcohol | 94410.0 | 4.0 | 19.483 | 0.147 | 3.417 |
| | Arachidyl ($C_{20}$) alcohol | 107336.0 | 4.0 | 21.070 | 0.135 | 4.182 |

*Experimental conditions for capillary microextraction and GC analysis are same as in FIGS. 16 (Phenols) and 17 (Alcohols and Amines).
**Detection limits were calculated for a signal-to-noise ratio (S/N) of 3 usiing the data presented in FIGS. 16 (Phenols) and 17 (Alcohols and Amines).

REFERENCES

Abe, I.; Kameyama, K.; Wasa, T.; *Chromatographia* 27, 631–633 (1989).

Aichholz, R. *J. High Resolut. Chomatogr.* 1990, 13, 71–73.

*Alltech Chromatography Catalog,* 1997, p. 172.

Altgelt, K. H.; Gouw, T. H., *Chromatography in Petroleum Analysis,* Marcel Dekker, N.Y., 1979.

An, M.; Haig, T.; Hatfield, P. *J. Chromatogr. A* 2001, 917, 245–250.

Arkles, B.; Steinmetz, J. R.; Zazyczny, J.; and Mehta, P. in *Silicon Compounds: Register and Review,* Huls, 1991, pp.65–73.

Arthur, C. L.; Killam, L. M.; Buchcholz, K. D.; Pawliszyn, J.; Berg, J. *Anal. Chem.* 1992, 64, 1960–66.

Arthur, C. L.; Killam, L. M.; Motlagh, S.; Potter, D. W.; Pawliszyn J. *Environ. Sci. Technol.* 1992, 26, 979–83

Arthur, C. L.; Pawliszyn, J. *Anal. Chem.* 1990, 62, 2145–2148.

Arthur, C. L.; Potter, D. W.; Buchholz, K. D.; Pawliszyn, J. *LC.GC.* 1994, 10, 656–61

Atik, M.; Luna, F. P.; Messaddeq, S. H.; Aegerter, M. A. *J. Sol. gel. Sci. Technol.* 1997, 8, 517–522.

Augusto, F.; Koziel, J.; Pawliszyn, J. *Anal. Chem.* 2001, 73, 481–486.

Aylott, J. W.; Richardson, D. J.; Russell, D. A. *Chem. Mater.* 1997, 9, 2261–2263.

Ballesteros, E.; Cardenas, S.; Gallego, M.; Valcarcel, M. *Anal Chem.* 1994, 66, 628–634.

Bartle, K. D.; Woolley, C. L.; Markides, K. E.; Lee, M. L.; Hanse, R. S. *J. High Resolut Chromatogr./Chromatogr. Commun* 1987, 10, 128–136.

Belardi, R. P.; Pawliszyn, J. *Water Pollut. Res. J. Canada* 1989, 24, 179–191.

Berezkin, V. G., Drugov, I. S., *Gas Chromatography in Air Pollution Analysis,* Elsevier, Amsterdam, 1991.

Berezkin, V. G.; Gavrichev, V. S.; Malik, A. *J. Liq. Chromatogr.* 1987, 10, 1707–1726.

Berezkin, V. G.; Shiryaeva, V. E.; Popova, T. P. *Zh. Analit. Khim.* 1992, 47, 825–831.

Berladi, R. P.; Pawliszyn, J. *Water Pollut. Res. J. Can.* 1989, 24,179–91.

Berladi, R. P.; Pawliszyn, J. *Water Pollut. Res. J. Can.* 1989, 24,179–91.

Blau, K.; King, G., Eds. *Handbook of Derivatives for Chromatography,* 2$^{nd}$ ed.; Heyden: London, 1993.

Blomberg, L.: Markides, K. E.; Wannman, T. *J. High Resolut Chromatogr. Chromatogr. Commun.* 1980, 3, 527.

Blomberg, L. G. *J. Microcol. Sep.* 1990, 2, 62–68.

Blomberg, L; Wannman, T. *J. Chromatogr.* 1978, 148, 379–387.

Blum, W. *J. High Resolut. Chromatogr./Chromatogr. Commun.* 1986, 9, 350–355.

Bouche, J.; Verzele, M. *J. Gas Chromatogr.* 1968, 6, 501–505.

Brinker, C. J.; Scherer, G. W. Sol-Gel Science, Academic Press, San Diego, Calif., 1990.

Brown, P. R.; Beebe, J. M.; Turcotte, Jr. Crit, Rev. *Anal. Chem.* 1989, 21, 193–208.

Buchholz, K. D.; Pawlyszyn, J. *Anal Chem.* 1994, 66, 160–167.

Buldt, A.; Kurst, U. *Anal Chem.* 1999, 71, 1893–1898.

Cabrera, K.; Lubda, D.; Eggenweiler, H.-M.; Minakuchi, H.; Nakanishi, K. *J. High Resol. Chromatogr.* 2000, 23, 93–99.

Chaput, F.; Dunn, B.; Fuqua, P.; Salloux, K. *J. Non. Cryst. Solids.* 1995, 188, 11–18.

Chen, Z.; Hobo, T. *Anal. Chem.* 2001, 73, 3348–3357.

Chong, S. L.; Wang, D.-.X.; Hayes, J. D.; Wilhite, B. W.; Malik, A. *Anal. Chem.* 1997, 69, 3889–3898.

Clement, R. E. (ed.), *Gas chromatography: Biochemical, Biomedical, and Clinical Applicants,* Wiley, N.Y., 1990.

Collinson, M. M.; Howeils, A. R. *Anal. Chem.* 2000, 72, 702A–709A.

Cortes, H. J.; Pfeiffer, C. D.; Richter, B. E.; Stevens, T. S. *J. High. Resolut. Chromatogr./Chromatogr. Commun.* 1987, 10, 446–448.

Coulibaly, K; Jeon I. J. *Food Rev. Int.* 1996, 12, 131–151.

de Fatima Alpendurada, M. *J. Chromatogr. A* 2000, 889, 3–14.

de Jong, C.; Badings, H. *J. High Resolut. Chromatogr.* 1990, 13, 94–98.

de Nijs; R. C. M.; Franken, J. J.; Dooper, R. P. M.; Rijks, J. A.; de Ruwe, J. J. J. M.; Schulting, F. L. *J. Chromatogr.* 1978, 167, 231–242.

Dislich, H. in *Sol-gel Technology for This Films, Fibers, Performs, Electronics, and Specialty Shapes,* (L.C. Klein ed., Noyes Publications, Park Ridge, N.J., USA, 1988), pp. 50–79.

Doesey, J. G.; Lister, A. S.; Wright, P. B.; Wendelken, S. C.; Chester, T. L. *Proc.* 19$^{th}$ *International Symposium on Capillary Chromatography and Electrophoresis,* Wintergree, Va., USA, May 18–22, 1997, pp. 62–63.

Dulay, M. T.; Kulkarni, R. P.; Zare, R. N. *Anal. Chem.* 1998, 70, 5103–5107.

Dutoit, D. C.; Schneider, M.; Baiker, A. *J. Catal.* 1995, 153, 165–176.

Eisert, R.; Pawliszyn, J. *Anal. Chem.* 1997, 69, 3140–3147.

Engelhardt, H.; Cunat-Walter, M. A. *J. Chromatogr.* 1995, 716, 27–33.

EPA Method 604. *Phenols in Federal Register,* Environmental Protection Agency: Friday, Oct. 6, 1984; pp. 58–66.

Ettre, L. C. *Chromatographia* 1948, 18, 477–488.

Ettre, L. S., Hinshaw, J. V. *Basic Relationship in Gas Chromatography,* Advanstar, Cleveland, USA, 1994, p.144.

Fabes, B. D.; Uhlmann D. R. *J. Am. Ceram. Soc.* 1990, 73, 978–988.

Ferioli, F.; Vezzalini, F.; Rustichelli, C.; Gamberini, G. *Chromatographia* 1995, 41, 61–65.

Fielding, M.; Farrimond, M. *Disinfection By-Products in Drinking Water. Current Issues,* Royal Society of Chemistry, Cambridge, UK, 1999.

Fields, S. M. *Anal. Chem.* 1996, 68, 2709–2712.

Fujimoto, C. *J. High Resol. Chromatogr.* 2000, 23, 89–92.

Gbatu, T. P.; Sutton, K. L.; Caruso, J. A. *Anal. Chim. Acta* 1999, 402, 67–79.

Golay, M. J. E., in Coates, V. J.; Noebels, H. J.; Faberson I. S. (eds.), *Gas Chromatography* (1957 Lansing Symposium), Academic Press, N.Y., 1958, pp.1–013.

Gou Y.; Pawliszyn, J. *Anal. Chem.* 2000, 72, 2774–2779.

Gou, Y.; Eisert, R.; Pawliszyn, J. *J. Chromatogr. A* 2000, 873, 137–147.

Gou, Y.; Tragas, C.; Lord, H.; Pawliszyn, J. *J. Micro Sep.* 2000, 12, 125–134.

Grob, K. Jr.; Grob, G.; Grob, K.; 1978, 156, 1–20.

Grob, K.; Grob, G.; Blum, W.; Walther, W. *J. Chromatogr.* 1982, 244, 197–204.

*Guidelines for Drinking Water Quality,* 2nd ed. WHO (World Health Organization): Geneva, 1993.

Guo, Y.; Colon, L. A. *Anal Chem.* 1995, 67 2511–2516.

Guo, Y.; Colon, L. A. *Chromatographia* 1996, 43, 477–483.

Guo, Y.; Colon, L. A. *J. Microcol. Sep.* 1995, 7, 485–491.

Guo, Y.; Imahori, G. A.; Colon, L. A. *J. Chromatogr. A.* 1996, 744, 17–29.

Hamlet, C.; Shende, C.; Kabir, A.; Malik, A. Work in progress.

Hartmann, H.; Burhenne, J.; Spiteller, M. *Fres. Environ. Bul.* 1998, 7, 96–103.

Haruvy, Y.; Gilath, I.; Maniewictz, M.; Eisenberg, N. *Chem. Mater.* 1997, 9, 2604–2615.

Hawthorne, S. B.; *Anal. Chem.* 1990, 62, 633A–642A.

Hayes, J. D.; Malik, A. *HPCE '97-Final Program* (Jan. 26–30, 1997, Anaheim, Calif., USA), pp. 80–81.

Hayes, J. D. "Sol-Gel Chemistry-Mediated Novel Approach to Column Technology for Electromigration Separations," Ph.D. dissertation, Department of Chemistry, University of South Florida, Tampa, Fla., USA, 2000.

Hayes, J. D.; Malik, A. *Anal. Chem.* 2000, 72, 4090–4099.

Hayes, J. D.; Malik, A. *Anal Chem.* 2001, 73, 987–996.

Hayes, J. D.; Malik, A. *J. Chromatogr. B* 1997, 695, 3–13.

Hirata, Y.; Pawliszyn, J. *J. Microcolumn Sep.* 1994, 6, 443–447.

Iler, R. K. *The Chemistry of Silica,* Wiley, New York, 1979.

In, M.; Gerardin, C.; Lambard, J.; Sanchez, C. *J. Sol. gel. Sci. Technol.* 1995, 5, 101–114.

Iwamoto, T.; Mackenzie, J. D. *J. Sol-gel Sci. Technol.* 1995, 4, 141–150.

Janak, K.; Horka, M.; Krejci, M. *J. Microcol. Sep.* 1991, 3, 115–120.

Janak, K.; Kahle, V.; Tesarik, K.; Horka, M. *J. High Resolut. Chromatogr./Chromatogr. Commun.* 1985, 8, 843–847.

Jiang, Z.-.; Zuo, Y.-. *Anal. Chem.* 2001, 73, 686–688.

Jinno, K.; Muramatsu, T.; Saito, Y.; Kiso, Y.; Magdic, S.; Pawliszyn J. *J. Chromatogr. A.* 1996, 754, 137–144.

Jones, S. A.; Wong, S.; Burlitch, J. M.; Viswanathan, S.; Kohlstedt, D. L. *Chem. Mater.* 1997, 9, 2567–2576.

Kataoka, H.; Lord, H. L.; Pawliszyn, J. *J. Anal. Toxicol.* 2000, 24, 257–265.

Kataoka, H.; Lord, H. L.; Pawliszyn, J. *J. Chromatogr. B* 1999, 731, 353–359.

Kataoka, H.; Narimatsu, S.; Lord, H.; Pawliszyn, J. *Anal Chem.* 1999, 71, 4237–4244.

Kataoka, H.; Pawliszyn, J. *Chromatographia* 1999, 50, 532–538.

Klein, L. C. *Sol-gel Technology for Thin Films, Fibers, Preforms, Electronics, and Specialty Shapes*; Noyes Publications: Park Ridge, N.J., USA, 1988 Koivusalmi, E.; Haatainen, E.; Root, A. *Anal Chem.* 1999, 71, 86–91.

Koster, E. H.; Bruins, C. H.; Wemes, C.; de Jong, G. J. *J. Sep. Sci.* 2001, 24, 116–122.

Kosuge, K.; Singh, P. S. *J. Phys. Chem. B* 1 999, 103, 3562–3569.

Koziel, J. A.; Noah, J.; Pawliszyn, J. *Environ. Sci. Technol.* 2001, 35, 1481–1486.

Lawrocki, J. *Chromatographia* 1991, 31, 177–205

Lee, M. L.; Kohn, R. C.; Woolley, C. L.; Bradshaw, J. S. *J. Chromatogr, Sci.* 1984, 22, 136–142.

Lee, M. L; Yang, F. J.; Bartle, K. D. *Open Tubular Column Gas Chromatography: Theory and Practice*, Wiley, N.Y., 1984.

Lev, O.; Bharathi, S.; Glezer, V.; Modestov, A.; Gun, J.; Rabinovich, L.; Sampath, S. *Chem. Mater.* 1997, 9, 2354–2375.

Li, D.; Park, J.; Oh, J.-R. *Anal. Chem.* 2001, 73, 3089–3095.

Liu, Y.; Shen, Y.; Lee, M. L. *Anal. Chem.* 1997, 69, 190–195.

Livage, J. In *Applications of Organometallic Chemistry in the Preparation and Processing of Advanced Materials*, Harrod, J. F., Laine, R. M. Eds.; Kluwer: Dordrecht, The Netherlands, 1995; pp. 3–25.

Livage, J.; Henry, M.; Sanchez, C. *Prog. Solid. St. Chem.* 1988, 18, 259–341.

Lobnik, A.; Wolfbeis, O. S. *Sens. Actuators B* 1998, 51, 203–207.

Lopez-Avila, V.; Bauer, K.; Milanes, J.; Beckert W. F. *J. AOAC Int.* 1993, 76, 864 880.

Louch, D.; Motlagh, S.; Pawliszyn J.; *Anal. Chem.* 1992, 64, 1187–1199.

Mackenzie, J. D. in *Hybrid Organic-Inorganic Composites* (ACS Symposium Series 585, American Chemical Society, Washington, D.C., 1995), pp. 227–236.

Majors, R. E. *LC*GC. Int.* 1997, 10, 93–101.

Malik, A.; Chong, S.-L. In *Applications of Solid-phase Microextraction*, Pawliszyn, J. Ed.; Royal Society of Chemistry (RSC): Cambridge (UK), 1999; pp.73–91.

Malik, A.; Hayes, J. D.; Wang, D. X.; Chong, S.-L.; Corbett, G. S.; Cramer, J. W.; *Proc. 19th International Symposium on Capillary Chromatography and Elctrophoresis*, Wintergreen, Va., USA, May 18–22, 1997, pp. 54–55. Martos, P. A.; Pawliszyn, J. *Anal. Chem.* 1998, 70, 2311–2320.

McComb, M. E.; Oleschuk, R. D.; Giller, E.; Gesser, H. D. *Talanta* 1997, 44, 2137–2143.

Medlar, J.; Kabir, A.; Malik, A. Work in Progress.

Mehrotra, R. C. *J. Non-Cryst. Solids* 1990, 121, 1–6.

*Merck Index,* 12th Edition, 1996, p. 9812.

Minnich, M.; Zimmerman, J. H.; Schumacher, B. A., *J. AOAC Int.* 1996, 1198–1204.

Mukherjee S., "Supercritical drying in structural and microstructural evaluation of gels: A critical review," in *Ultrasound Processing of Advanced Ceramics* (Mackenzie, J. D. and Ulrich, D. R., eds., Wiley, N.Y., 1988), pp. 747–759 Muller, L.; Gorecki, T.; Pawliszyn, J. *Fres. J. Anal Chem.* 1999, 364, 610–616.

Nakanishi, K.; Minakuchi, H.; Soga, N.; Tanaka, N. *J. Sol. gel. Sci. Technol.* 1997, 8, 547–552.

Narang, P.; Colon, L. A. *J. Chromatogr. A.* 1997, 773, 65–72.

Nawrocki, J. *J. Chromatogr. A* 1996, 749, 157–163.

Novak, B. M. *Adv. Mater.* 1993, 5, 422–433.

Oesterheldt, G.; Pozeg, M.; Bubendorf, A.; Bartoldus, D. *Fres. Z. Anal. Chem.* 1985, 321, 553–555.

Palkar, V. R. *Nanostructured Mater.* 1999, 11, 369–374.

Pawliszyn, J. *Solid Phase Microextraction. Theory and Practice*, Wiley: N.Y., 1997.

Pawliszyn, J. *J. Chromatogr. Sci.* 2000, 37, 270–270.

Poole, C. F.; Poole, S. K., in E. Heftman (ed.) *Chromatography*, 5$^{th}$ Edition, Part A: Fundamentals and Techniques (J. Chromatogr. Libr. Vol. 51 A, Amsterdam, 1992), ch. 9

Poole, S. K; Dean, T. A.: Oudsema J. W.; and Poole, C. F.; *Anal. Chim. Acta.* 1990, 236, 3–42.

Potter, D. W.; Pawliszyn, J. *Environ. Sci. Technol.* 1994, 28, 298–305.

Potter, D. W.; Pawliszyn, J. *J. Chromatogr.* 1992, 625, 247–55.

Prakash, S. S.; Brinker C. J.; Hurd, A. J.; Rao, S. M. *Nature* 1995, 374–439–443.

Pursch, M.; Jager, A.; Schneller, T.; Brindle, R.; Albert, K.; Lindner, E. *Chem. Mater.* 1996, 8, 1245–1249.

Rabinovich, E. M. In *Sol Gel Technology for Thin Films, fibers, Preforms, Electronics, and Specialty Shapes*, Klein, L. C. Ed.; Noyes Publications: Park Ridge, N.J., 1988; pp. 260–294.

Ramsey, J. D. F., "Sol-gel Processing" in *Controlled Particle, Droplet and Bubble Formation*, (D. J. Wedlock ed., Butterworth, U. K., 1994), pp.1–37 Reighard, T. S.; Olesik, S. V.; *Crit. Rev. Anal Chem.* 1996, 26, 61–99.

Reisfeld, R.; Jorgenson, C. K. (eds.), *Spectroscopy, Chemistry, and Applications of Sol-gel Glasses*, Springer-Verlag, Berlin, 1992.

Reynolds, K. J.; Colon, L. A. *J. Liq. Chromatogr. & Rel. Technol.* 2000, 23, 161–173.

Richter, B. E.; Jones, B. A.; Ezzel, J. L.; Porter N. L.; Abdalovic N.; Pohl, C. *Anal Chem.* 1996, 1033–1039.

Richter, B. E.; Kuci, J. C.; Park, N. J.; Crowley, S. J.; Bradshaw, J. S.; Lee, M. L. *J. High Resolut. Chromatogr./Chromatogr. Commun.* 1986, 6, 371–373.

Rodriguez, I.; Llompart, M. P.; Cela, R. *J. Chromatogr. A* 2000, 885, 291–304.

Rodriguez, S. A.; Colon, L. A. *Anal. Chim. Acta* 1999, 397, 207–215.

Rodriguez, S. A.; Colon, L. A. *Chem. Mater.* 1999, 11, 754–762.

Roed, L.; Lundanes, E.; Greibrokk, *J. Chromatogr. A* 2000, 890, 347–353.

Roed, L.; Lundanes, E.; Greibrokk, T. *J. Micro Sep.* 2000, 12, 561–567.

Rotzsche, H. *Stationary Phases in Gas Chromatography*; Elsevier Scientific Publishing Company: Amsterdam, The Netherlands, 1991.

Sakka, S.; Yoko, T. In *Chemistry, Spectroscopy, and Applications*, Reisfeld, R., Jorgenson, C. K. Eds.; Springer-Verlag: Berlin, 1992; pp. 89–118.

Sanchez, C.: Ribot, F. *New J. Chem.* 18, 1007–1047 (1994).

Scheppers Wercinski, S. A. *Solid-phase Microextraction: A Practical Guide*, Marcel Dekker: N.Y., 1999.

Scherer, G. W., "Aging and drying of gels," *J. Non-Cryst. Solids* 1988, 100, 77–92.

Schomburg, G.; Husmann, H.; Borwitsky, H., *Chromatographia* 1979, 12, 651–660.

Senevirante, J.; Cox, J. A. *Talanta* 2000, 52, 801–806.

Sharp, K. G. *J. Sol-gel Sci. Technol.* 1994, 2, 35–41.

Shende, C.; Kabir, A.; Hamlet, C.; Malik, A. *Manuscript in preparation.*

Silva, R. B.; Gushikem, Y.; Collins, C. H. *J. Sep. Sci.* 2001, 24, 49–54.

Stark, F. O.; Johnson, O. K.; Vogel, E. G.; Chafee, R. G.; Lacefield, R. M. *J. Phys. Chem.* 1968, 72, 2750–2754.

Sumpter, S. R.; Woolley, C. L.; Hunag, E. C.; Markides, K. E.; Lee, M. L. *J. Chromatogr.* 1990, 517, 503–519.

SUPELCO Catalog 2001: *Chromatography Products for Analysis and Purification*, Aldrich-Sigma Co.: USA, 2001; p.259.

Supelco Corp., Bellefonte, Pa. *Manufacturer data sheet.* 1996.

Tang, Q.; Xin, B.; Le, M. L. *J. Chromatogr. A* 1999, 837, 35–50.

Tebbett, I. (Ed.), *Gas Chromatography in Forensic Science*, E. Horwood, N.Y., 1991.

van Deemter, J. J.; Zuiderweg, F. J.; Klinkenberg, A. *Chem. Eng. Sci.* 1956, 5, 271–289.

van der Vis, E.; Mazereeuw, M.; Tjaden, U. R.; Irth, H.; van der Greef, J. *J. Chromatogr. A.* 1994, 333–341.

Vicanova, J.; Tvrzicka, E.; Stulik, K. *J. Chromatogr. B* 1994, 656, 45–50.

Vorotilov, K. A.; Petrovsky, V. I.; Vasiliev, V. A.; Sobolevsky, M. V. *J. Sol-gel Sci. Technol.* 1997, 8, 581–584.

Walsh, D.; Whilton, N. T. *Chem. Mater.* 1997, 9, 2300–2310.

Wang, D. X. *Sol-gel Chemistry-Mediated Novel Approach to Column Technology for High-Resolution Capillary Gas Chromatography*, Ph.D. Dissertation, University of South Florida, Department of Chemistry: Tampa, Fla., 2000.

Wang, D.-X.; Chong, S.-L.; Malik, A. *Anal. Chem.* 1997, 69, 4566–4576.

Wang, D; Malik, A. *Proc. 18$^{th}$ Intl. Symp. Cap. Chromatogr.* (May 20–24, 1996, Riva del Garda, Italy), P. Sandra & G. Devos (eds.), Huthig Publishers: Germany, 1996, pp. 505–513.

Wang, Z. Y.; Xiao, C. H.; Wu, C. Y.; Wu, C.; Han, H. *J. Chromatogr. A* 2000, 893, 157–168.

Welxch, T.; Teichmann, U., *J. High Resolut. Chromatogr.,* 1991, 14, 153–159.

Westwood, S. A. (Ed.), *Supercritical Fluid Extraction and Its Use in Chromatographic Sample*, CRC Press, Boca Raton, Fla., USA 1993.

Wilkes, G. L.; Arler, B.; Huang, H. H. *Polymer Prep.* 1985, 26, 300.

Woolley, C. L.; Koihn, R. C.; Richter, B. E.; Lee, M. L. *J. High Resolut. Chromatogr./Chromatogr. Commun.* 1984, 7, 329–332.

Woolley, C. L.; Markides, K. E.; Lee, M. L. *J. Chromatogr.* 1986, 367, 9–22.

Woolley, C. L; Markides, K. E.; Lee, M. L.; Bartle, K. D. *J. High Resolut. Chromatogr./Chromatogr. Commun.* 1986, 9, 506–514.

Wright, B. W.; Peaden, P. A.; Lee, M. L.; Stark, T. J. *J. Chromatogr.* 1982, 248, 17–34.

Wu, J.; Lord, H. L.; Pawliszyn, J.; Kataoka, H. *J. Micro. Sep.* 2000, 12, 255–266.

Wu, J.; Mester, Z.; Pawliszyn, J. *Anal. Chim. Acta* 2000, 424, 211–222.

Wu, J.; Pawliszyn, J. *Anal. Chem.* 2001, 73, 55–63.

Wu, J.; Pawliszyn, J. *J. Chromatogr. A* 2001, 909, 37–52.

Yakabe, Y.; Sudoh, Y.; Takahata, Y. *J. Chromatogr.* 1991, 558, 323–327.

Zapf, A.; Stan, H. J. *J. High Resol. Chromatogr.* 1999, 22, 83–88.

Zeng, Z.; Qiu, W.; Huang, Z. *Anal. Chem.* 2001, 73, 2429–2436.

Zhang, J.; Zhang, L.; Ilacqua, V. *Environ. Sci. Technol.* 2000, 34, 2601–2607.

Zhang, Z.; Yang, M. J.; Pawliszyn, J. *Anal. Chem.* 1994, 66, 844A–853A.

Zlotorzynski, A. *Crit. Rev. Anal. Chem.* 1995, 25, 43–76.

What is claimed is:

1. A method of preconcentrating trace analytes, comprising to steps of:
    processing a hollow capillary by hydrothermal treatment;
    filling the capillary with a sol-gel extraction medium, wherein the sol-gel extraction medium is chemically bound to inner walls of the hollow capillary to form a sol-gel extraction medium-loaded capillary; and
    exposing the loaded capillary to a sample containing at least one target analyte, wherein the target analyte becomes disposed inside the loaded capillary.

2. A method according to claim 1, wherein said exposing step comprises directing said sample through said coated capillary.

3. A method according to claim 1, wherein said sol-gel extraction medium comprises a sol-gel coating.

4. A method according to claim 1, wherein said sol-gel extraction medium comprises a porous sol gel monolithic bed.

5. A method according to claim 1, wherein an organic component of said sol-gel is selected from the group consisting of sol-gel active forms and/or derivatives of poly (ethylene glycol), poly(methylphenylsiloxane), poly (dimethyldiphenylsiloxane) poly(dimethylsiloxane), poly (methylcyanopropylsiloxane) octadecylsilane, octylsilane, crown ethers, cyclodextrins, calixarenes, dendrimers, poly (styrene), poly(styrene-divinylbenzene), poly(acrylate), and molecularly imprinted polymers.

6. A method according to claim 1, further including the step of desorbing said analyte from said sol-gel extraction medium to provide extracted analyte.

7. A method according to claim 6, wherein said desorbing step comprises thermal desorbing.

8. A method according to claim 6, further including the step of applying said extracted analyte to a GC capillary column.

9. A method according to claim 6, further including the step of directing said extracted analyte to a liquid phase separation system.

10. A method according to claim 1, thither including the step of preconditioning sol-gel extraction medium prior to said exposing step.

11. A method according to claim 10, wherein said preconditioning step comprises heating and purging an inert gas over sol-gel extraction medium.

* * * * *

UNITED STATES PATENT AND TRADEMARK OFFICE
CERTIFICATE OF CORRECTION

PATENT NO. : 6,783,680 B2
DATED : August 31, 2004
INVENTOR(S) : Abdul Malik

It is certified that error appears in the above-identified patent and that said Letters Patent is hereby corrected as shown below:

Column 29,
Line 15, "to" should be changed to -- the --

Column 30,
Line 24, "thither" should be changed to -- further --

Signed and Sealed this

Thirtieth Day of November, 2004

JON W. DUDAS
*Director of the United States Patent and Trademark Office*